United States Patent
Schaller et al.

(10) Patent No.: US 7,763,040 B2
(45) Date of Patent: *Jul. 27, 2010

(54) TISSUE CONNECTOR APPARATUS AND METHODS

(75) Inventors: Laurent Schaller, Los Altos, CA (US); Charles T. Maroney, Portola Valley, CA (US); Phillip Drews, San Jose, CA (US); Isidro Matias Gandionco, Fremont, CA (US); John Nguyen, San Jose, CA (US)

(73) Assignee: Medtronic, Inc., Minneapolis, MN (US)

( * ) Notice: Subject to any disclaimer, the term of this patent is extended or adjusted under 35 U.S.C. 154(b) by 1324 days.

This patent is subject to a terminal disclaimer.

(21) Appl. No.: 10/364,064

(22) Filed: Feb. 10, 2003

(65) Prior Publication Data
US 2003/0125755 A1 Jul. 3, 2003

Related U.S. Application Data

(63) Continuation of application No. 09/090,305, filed on Jun. 3, 1998, now Pat. No. 6,641,593.

(51) Int. Cl.
*A61B 17/08* (2006.01)
*A61B 17/04* (2006.01)

(52) U.S. Cl. ...................... 606/153; 606/232

(58) Field of Classification Search ........... 606/151, 606/157, 158, 219, 222, 153, 155, 191, 213, 606/232, 142, 198, 148, 205, 231; 607/132
See application file for complete search history.

(56) References Cited

U.S. PATENT DOCUMENTS 43,098 A 6/1864 Cooper

| 636,728 A | 11/1899 | Kindel |
| 655,190 A | 8/1900 | Bramson |
| 1,087,186 A | 2/1914 | Scholfield |

(Continued)

FOREIGN PATENT DOCUMENTS

DE 21 99 99 3/1910

(Continued)

OTHER PUBLICATIONS

Emery, R. W., et al., "Suture techniques for MIDCAB Surgery," Chapter 12 in *Techniques for Minimally Invasive Direct Coronary Artery Bypass (MIDCAB) Surgery*. R.W. Emery ed., Hanley & Belfus, Inc.: Philadelphia, PA, pp. 87-91 (1997).

(Continued)

*Primary Examiner*—Julian W Woo
(74) *Attorney, Agent, or Firm*—Mike Jaro; Jeffrey J. Hohenshell

(57) ABSTRACT

A tissue connector assembly comprising a clip movable between an open configuration and a closed configuration and a mechanical restraining device attached to the clip for restraining the clip in its open configuration. A needle may be releasably attached to the clip. A method for connecting tissues is also disclosed. The method includes inserting a clip through tissue with the clip being biased in an open position by a restraining device secured to the clip, and removing the restraining device from the clip.

43 Claims, 12 Drawing Sheets

U.S. PATENT DOCUMENTS

| | | | |
|---|---|---|---|
| 1,167,014 A | 1/1916 | O'Brien | |
| 1,539,221 A | 5/1925 | John | |
| 1,583,271 A | 5/1926 | Biro | |
| 1,625,602 A | 4/1927 | Gould et al. | |
| 1,867,624 A | 7/1932 | Hoffman | |
| 2,201,610 A | 5/1940 | Dawson | |
| 2,240,330 A | 4/1941 | Flagg et al. | |
| 2,256,382 A | 9/1941 | Dole | |
| 2,264,679 A | 12/1941 | Ravel | |
| 2,413,142 A | 12/1946 | Jones et al. | |
| 2,430,293 A | 11/1947 | Howells | |
| 2,505,358 A | 4/1950 | Gusberg et al. | |
| 2,516,710 A | 7/1950 | Mascolo | |
| 2,715,486 A | 8/1955 | Marcoff-Moghadam et al. | |
| 2,890,519 A | 6/1959 | Storz, Jr. | |
| 2,940,452 A | 6/1960 | Smialowski | |
| 3,055,689 A | 9/1962 | Jorgensen | |
| 3,057,355 A | 10/1962 | Smialowski | |
| 3,082,426 A | 3/1963 | Miles | |
| 3,125,095 A * | 3/1964 | Kaufman et al. | 607/132 |
| 3,143,742 A | 8/1964 | Cromie | |
| 3,150,379 A | 9/1964 | Brown | |
| 3,180,337 A | 4/1965 | Smialowski | |
| 3,249,104 A | 5/1966 | Hohnstein | |
| 3,274,658 A | 9/1966 | Pile | |
| 3,452,742 A | 7/1969 | Muller | |
| 3,462,802 A | 8/1969 | Merser | |
| 3,506,012 A | 4/1970 | Brown | |
| 3,509,882 A | 5/1970 | Blake | |
| 3,547,103 A | 12/1970 | Cook | |
| 3,570,497 A | 3/1971 | Lemole | |
| 3,608,095 A | 9/1971 | Barry | |
| 3,638,654 A | 2/1972 | Akuba | |
| 3,656,185 A | 4/1972 | Carpentier | |
| RE27,391 E | 6/1972 | Merser | |
| 3,753,438 A | 8/1973 | Wood et al. | |
| 3,776,237 A | 12/1973 | Hill et al. | |
| 3,802,438 A | 4/1974 | Wolvek | |
| 3,825,009 A | 7/1974 | Williams | |
| 3,837,345 A | 9/1974 | Matar | |
| 3,874,388 A | 4/1975 | King et al. | |
| 3,875,648 A | 4/1975 | Bone | |
| 3,905,403 A | 9/1975 | Smith et al. | |
| 3,908,662 A | 9/1975 | Razgulov et al. | |
| 3,910,281 A | 10/1975 | Kletschka et al. | |
| 3,958,576 A | 5/1976 | Komiya | |
| 3,976,079 A | 8/1976 | Samuels | |
| 3,995,619 A | 12/1976 | Glatzer | |
| 4,006,747 A | 2/1977 | Kronenthal et al. | |
| 4,018,228 A | 4/1977 | Goosen | |
| 4,038,725 A | 8/1977 | Keefe | |
| 4,042,979 A | 8/1977 | Angell | |
| 4,073,179 A | 2/1978 | Hickey et al. | |
| 4,103,690 A | 8/1978 | Harris | |
| 4,111,206 A | 9/1978 | Vishnevsky et al. | |
| 4,129,059 A | 12/1978 | Van Eck | |
| 4,140,125 A | 2/1979 | Smith | |
| 4,170,990 A | 10/1979 | Baumgart et al. | |
| 4,185,636 A | 1/1980 | Gabbay et al. | |
| 4,192,315 A | 3/1980 | Hilzinger et al. | |
| 4,214,587 A | 7/1980 | Sakura | |
| 4,217,902 A | 8/1980 | March | |
| 4,243,048 A | 1/1981 | Griffin | |
| 4,324,248 A | 4/1982 | Perlin | |
| 4,341,226 A * | 7/1982 | Peters | 607/132 |
| 4,345,601 A * | 8/1982 | Fukuda | 606/147 |
| 4,352,358 A | 10/1982 | Angelchik | |
| 4,366,819 A | 1/1983 | Kaster | |
| 4,396,139 A | 8/1983 | Hall et al. | |
| 4,416,266 A | 11/1983 | Baucom | |
| 4,456,017 A | 6/1984 | Miles | |
| 4,465,071 A | 8/1984 | Samuels et al. |
| 4,470,415 A | 9/1984 | Wozniak |
| 4,470,533 A | 9/1984 | Schuler |
| 4,474,181 A | 10/1984 | Schenck |
| 4,485,816 A | 12/1984 | Krumme |
| 4,492,229 A | 1/1985 | Grunwald |
| 4,522,207 A | 6/1985 | Klieman et al. |
| 4,523,592 A | 6/1985 | Daniel |
| 4,532,927 A | 8/1985 | Miksza |
| 4,535,764 A | 8/1985 | Ebert |
| 4,549,545 A | 10/1985 | Levy |
| 4,553,542 A | 11/1985 | Schenck et al. |
| 4,576,605 A | 3/1986 | Kaidash et al. |
| 4,586,502 A | 5/1986 | Bedi et al. |
| 4,586,503 A | 5/1986 | Kirsch et al. |
| 4,593,693 A | 6/1986 | Schenck |
| 4,595,007 A | 6/1986 | Mericle |
| 4,612,932 A | 9/1986 | Caspar et al. |
| 4,622,970 A | 11/1986 | Wozniak |
| 4,624,255 A | 11/1986 | Schenck et al. |
| 4,637,380 A | 1/1987 | Orejola |
| 4,641,652 A | 2/1987 | Hutterer et al. |
| 4,665,906 A | 5/1987 | Jervis |
| 4,665,917 A | 5/1987 | Clanton et al. |
| 4,683,895 A | 8/1987 | Pohndorf |
| 4,706,362 A | 11/1987 | Strausburg |
| 4,719,917 A | 1/1988 | Barrows et al. |
| 4,719,924 A | 1/1988 | Crittenden et al. |
| 4,730,615 A | 3/1988 | Sutherland et al. |
| 4,732,151 A | 3/1988 | Jones |
| 4,809,695 A | 3/1989 | Gwathmey et al. |
| 4,820,298 A | 4/1989 | Leveen et al. |
| 4,844,318 A | 7/1989 | Kunreuther |
| 4,873,975 A | 10/1989 | Walsh et al. |
| 4,890,615 A | 1/1990 | Caspari et al. |
| 4,896,668 A | 1/1990 | Popoff et al. |
| 4,899,744 A | 2/1990 | Fujitsuka et al. |
| 4,901,721 A | 2/1990 | Hakki |
| 4,923,461 A | 5/1990 | Caspari et al. |
| 4,924,866 A | 5/1990 | Yoon |
| 4,926,860 A | 5/1990 | Stice et al. |
| 4,929,240 A | 5/1990 | Kirsch et al. |
| 4,930,674 A | 6/1990 | Barak |
| 4,932,955 A | 6/1990 | Merz et al. |
| 4,935,027 A | 6/1990 | Yoon |
| 4,950,015 A | 8/1990 | Nejib et al. |
| 4,950,283 A | 8/1990 | Dzubow et al. |
| 4,950,285 A | 8/1990 | Wilk |
| 4,957,498 A | 9/1990 | Caspari et al. |
| 4,983,176 A | 1/1991 | Cushman et al. |
| 4,990,152 A | 2/1991 | Yoon |
| 4,991,567 A | 2/1991 | McCuen et al. |
| 4,994,069 A | 2/1991 | Ritchart et al. |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,007,920 A | 4/1991 | Torre |
| 5,011,481 A | 4/1991 | Myers et al. |
| 5,020,713 A | 6/1991 | Kunreuther |
| 5,026,379 A | 6/1991 | Yoon |
| 5,032,127 A | 7/1991 | Frazee et al. |
| 5,035,692 A | 7/1991 | Lyon et al. |
| 5,035,702 A | 7/1991 | Taheri |
| 5,042,707 A | 8/1991 | Taheri |
| 5,047,047 A | 9/1991 | Yoon |
| 5,053,047 A | 10/1991 | Yoon |
| 5,064,431 A | 11/1991 | Gilbertson et al. |
| 5,074,874 A | 12/1991 | Yoon et al. |
| 5,088,692 A | 2/1992 | Weiler |
| 5,100,418 A | 3/1992 | Yoon et al. |
| 5,100,421 A | 3/1992 | Christoudias |
| 5,104,407 A | 4/1992 | Lam et al. |

| | | | | | |
|---|---|---|---|---|---|
| 5,119,983 A | 6/1992 | Green et al. | 5,445,167 A | 8/1995 | Yoon et al. |
| 5,123,913 A | 6/1992 | Wilk et al. | 5,445,644 A | 8/1995 | Pietrafitta et al. |
| 5,127,413 A | 7/1992 | Ebert | 5,450,860 A | 9/1995 | O'Connor |
| 5,129,913 A | 7/1992 | Ruppert | 5,451,231 A | 9/1995 | Rabenau et al. |
| 5,152,769 A | 10/1992 | Baber | 5,452,733 A | 9/1995 | Sterman et al. |
| 5,154,189 A | 10/1992 | Oberlander | 5,454,834 A | 10/1995 | Boebel et al. |
| 5,158,566 A | 10/1992 | Pianetti | 5,456,246 A | 10/1995 | Schmieding et al. |
| 5,171,250 A | 12/1992 | Yoon | 5,462,561 A | 10/1995 | Voda |
| 5,171,252 A | 12/1992 | Friedland | 5,474,557 A | 12/1995 | Mai |
| 5,174,087 A | 12/1992 | Bruno | 5,480,405 A | 1/1996 | Yoon |
| 5,178,634 A | 1/1993 | Ramos Martinez | 5,486,187 A | 1/1996 | Schenck |
| 5,192,294 A | 3/1993 | Blake | 5,486,197 A | 1/1996 | Le et al. |
| 5,196,022 A | 3/1993 | Bilweis | 5,488,958 A | 2/1996 | Topel et al. |
| 5,196,023 A * | 3/1993 | Martin ............ 606/148 | 5,496,334 A | 3/1996 | Klundt et al. |
| 5,201,880 A | 4/1993 | Wright et al. | 5,499,990 A | 3/1996 | Schulken et al. |
| 5,207,694 A | 5/1993 | Broome | 5,500,000 A | 3/1996 | Feagin et al. |
| 5,217,027 A | 6/1993 | Hermens | 5,522,884 A | 6/1996 | Wright |
| 5,219,358 A | 6/1993 | Bendel et al. | 5,527,342 A | 6/1996 | Pietrzak et al. |
| 5,221,259 A | 6/1993 | Weldon et al. | 5,533,236 A | 7/1996 | Tseng |
| 5,222,961 A | 6/1993 | Nakao et al. | 5,538,509 A | 7/1996 | Dunlap et al. |
| 5,222,976 A | 6/1993 | Yoon | 5,545,214 A | 8/1996 | Stevens |
| 5,234,447 A | 8/1993 | Kaster et al. | 5,549,619 A | 8/1996 | Peters et al. |
| 5,236,440 A | 8/1993 | Hlavacek | 5,556,411 A | 9/1996 | Taoda et al. |
| 5,242,456 A | 9/1993 | Nash et al. | 5,562,685 A | 10/1996 | Mollenauer et al. |
| 5,242,457 A | 9/1993 | Akopov et al. | 5,569,205 A | 10/1996 | Hart et al. |
| 5,246,443 A | 9/1993 | Mai | 5,569,274 A | 10/1996 | Rapacki et al. |
| 5,250,053 A | 10/1993 | Snyder | 5,569,301 A | 10/1996 | Granger et al. |
| 5,250,071 A * | 10/1993 | Palermo ............ 606/198 | 5,571,119 A | 11/1996 | Atala |
| 5,258,011 A | 11/1993 | Drews | 5,571,175 A | 11/1996 | Vanney et al. |
| 5,261,917 A | 11/1993 | Hasson et al. | 5,582,616 A | 12/1996 | Bolduc et al. |
| 5,269,783 A | 12/1993 | Sander | 5,582,619 A * | 12/1996 | Ken ............ 606/198 |
| 5,269,809 A | 12/1993 | Hayhurst et al. | 5,584,879 A | 12/1996 | Reimold et al. |
| 5,282,825 A | 2/1994 | Muck et al. | 5,586,983 A | 12/1996 | Sanders et al. |
| 5,290,289 A | 3/1994 | Sanders et al. | 5,591,179 A | 1/1997 | Edelstein |
| 5,304,117 A | 4/1994 | Wilk | 5,593,414 A | 1/1997 | Shipp et al. |
| 5,304,204 A | 4/1994 | Bregen | 5,593,424 A | 1/1997 | Northrup, III |
| 5,306,296 A | 4/1994 | Wright et al. | 5,597,378 A | 1/1997 | Jervis |
| 5,312,436 A | 5/1994 | Coffey et al. | 5,601,571 A | 2/1997 | Moss |
| 5,314,468 A | 5/1994 | Ramos Martinez | 5,601,572 A | 2/1997 | Middleman et al. |
| 5,330,503 A | 7/1994 | Yoon | 5,601,600 A | 2/1997 | Ton |
| 5,334,196 A | 8/1994 | Scott et al. | 5,603,718 A | 2/1997 | Xu |
| 5,336,233 A | 8/1994 | Chen | 5,609,608 A | 3/1997 | Benett et al. |
| 5,336,239 A | 8/1994 | Gimpelson | 5,628,757 A | 5/1997 | Hasson |
| 5,346,459 A | 9/1994 | Allen | 5,630,540 A | 5/1997 | Blewett |
| 5,350,419 A * | 9/1994 | Bendel et al. ............ 607/132 | 5,632,752 A | 5/1997 | Buelna |
| 5,350,420 A | 9/1994 | Cosgrove et al. | 5,632,753 A | 5/1997 | Loeser |
| 5,353,804 A | 10/1994 | Kornberg et al. | 5,643,295 A | 7/1997 | Yoon |
| 5,355,897 A | 10/1994 | Pietrafitta et al. | 5,643,305 A | 7/1997 | Al-Tameem |
| 5,356,424 A | 10/1994 | Buzerak et al. | 5,645,568 A | 7/1997 | Chervitz et al. |
| 5,362,294 A * | 11/1994 | Seitzinger ............ 606/231 | 5,653,716 A | 8/1997 | Malo et al. |
| 5,364,406 A | 11/1994 | Sewell | 5,653,718 A | 8/1997 | Yoon |
| 5,366,459 A | 11/1994 | Yoon | 5,658,312 A | 8/1997 | Green et al. |
| 5,366,462 A | 11/1994 | Kaster et al. | 5,660,186 A | 8/1997 | Bachir |
| 5,366,479 A | 11/1994 | McGarry et al. | 5,665,109 A | 9/1997 | Yoon |
| 5,374,268 A | 12/1994 | Sander | 5,669,918 A | 9/1997 | Balazs et al. |
| 5,376,096 A | 12/1994 | Foster | 5,676,670 A | 10/1997 | Kim |
| 5,376,101 A * | 12/1994 | Green et al. ............ 606/232 | 5,683,417 A | 11/1997 | Cooper |
| 5,382,259 A | 1/1995 | Phelps et al. | 5,690,662 A | 11/1997 | Chiu et al. |
| 5,383,904 A | 1/1995 | Totakura et al. | 5,695,504 A | 12/1997 | Gifford, III et al. |
| 5,387,227 A | 2/1995 | Grice | 5,695,505 A | 12/1997 | Yoon |
| 5,403,331 A | 4/1995 | Chesterfield | 5,697,913 A | 12/1997 | Sierocuk et al. |
| 5,403,333 A | 4/1995 | Kaster et al. | 5,697,943 A | 12/1997 | Sauer et al. |
| 5,403,338 A | 4/1995 | Milo | 5,700,270 A | 12/1997 | Peyser et al. |
| 5,403,346 A | 4/1995 | Loeser | 5,700,271 A | 12/1997 | Whitfield et al. |
| 5,413,584 A | 5/1995 | Schulze | 5,702,412 A | 12/1997 | Popov et al. |
| 5,417,684 A | 5/1995 | Jackson et al. | 5,707,362 A | 1/1998 | Yoon |
| 5,417,700 A | 5/1995 | Egan | 5,707,380 A | 1/1998 | Hinchliffe et al. |
| 5,423,821 A | 6/1995 | Pasque | 5,709,693 A | 1/1998 | Taylor |
| 5,431,666 A | 7/1995 | Sauer et al. | 5,709,695 A | 1/1998 | Northrup, III |
| 5,437,680 A | 8/1995 | Yoon | 5,715,987 A | 2/1998 | Kelley et al. |
| 5,437,681 A | 8/1995 | Meade et al. | 5,720,755 A | 2/1998 | Dakov |
| 5,437,685 A | 8/1995 | Blasnik | 5,725,539 A | 3/1998 | Matern |
| 5,439,479 A | 8/1995 | Shichman et al. | 5,725,542 A | 3/1998 | Yoon |

| | | | | | | |
|---|---|---|---|---|---|---|
| 5,728,135 A | 3/1998 | Bregen et al. | 5,989,268 A | 11/1999 | Pugsley, Jr. et al. | |
| 5,732,872 A | 3/1998 | Bolduc et al. | 5,989,276 A | 11/1999 | Houser et al. | |
| 5,735,290 A | 4/1998 | Sterman et al. | 5,989,278 A | 11/1999 | Mueller | |
| 5,746,753 A | 5/1998 | Sullivan et al. | 5,993,468 A | 11/1999 | Rygaard | |
| 5,755,778 A | 5/1998 | Kleshinski | 5,997,556 A | 12/1999 | Tanner | |
| 5,766,189 A | 6/1998 | Matsumo | 6,001,110 A * | 12/1999 | Adams | 606/151 |
| 5,769,870 A | 6/1998 | Salahich et al. | 6,007,544 A | 12/1999 | Kim | |
| 5,779,718 A | 7/1998 | Green et al. | 6,010,531 A | 1/2000 | Donlon et al. | |
| 5,782,397 A | 7/1998 | Koukline | 6,013,084 A | 1/2000 | Ken et al. | |
| 5,782,844 A * | 7/1998 | Yoon et al. ................. 606/139 | 6,022,367 A | 2/2000 | Sherts | |
| 5,797,920 A | 8/1998 | Kim | 6,024,748 A | 2/2000 | Manzo et al. | |
| 5,797,933 A | 8/1998 | Snow et al. | 6,032,849 A | 3/2000 | Mastri et al. | |
| 5,797,934 A | 8/1998 | Rygaard | 6,033,419 A | 3/2000 | Hamblin, Jr. et al. | |
| 5,797,960 A | 8/1998 | Stevens et al. | 6,036,699 A | 3/2000 | Andreas et al. | |
| 5,799,661 A | 9/1998 | Boyd et al. | 6,036,703 A | 3/2000 | Evans et al. | |
| 5,799,857 A | 9/1998 | Robertson et al. | 6,036,710 A | 3/2000 | McGarry et al. | |
| 5,810,848 A | 9/1998 | Hayhurst | 6,042,607 A | 3/2000 | Williamson et al. | |
| 5,810,851 A | 9/1998 | Yoon | 6,056,751 A | 5/2000 | Fenton | |
| 5,810,853 A | 9/1998 | Yoon | 6,063,070 A | 5/2000 | Eder | |
| 5,810,882 A | 9/1998 | Bolduc et al. | 6,066,148 A | 5/2000 | Rygaard | |
| 5,817,113 A | 10/1998 | Gifford, III et al. | 6,074,401 A | 6/2000 | Gardiner et al. | |
| 5,820,631 A | 10/1998 | Nobles | 6,074,418 A | 6/2000 | Buchanan et al. | |
| 5,824,002 A | 10/1998 | Gentelia et al. | 6,077,291 A | 6/2000 | Das | |
| 5,824,008 A | 10/1998 | Bolduc et al. | 6,080,114 A | 6/2000 | Russin | |
| 5,827,265 A | 10/1998 | Glinsky et al. | 6,083,237 A | 7/2000 | Huitema et al. | |
| 5,827,316 A | 10/1998 | Young et al. | 6,106,538 A | 8/2000 | Shiber | |
| 5,830,221 A | 11/1998 | Stein et al. | 6,110,188 A | 8/2000 | Narciso | |
| 5,830,222 A | 11/1998 | Makower | 6,113,611 A | 9/2000 | Allen et al. | |
| 5,833,698 A | 11/1998 | Hinchliffe | 6,113,612 A | 9/2000 | Swanson et al. | |
| 5,849,019 A | 12/1998 | Yoon | 6,120,524 A | 9/2000 | Taheri | |
| 5,851,216 A | 12/1998 | Allen | 6,132,438 A * | 10/2000 | Fleischman et al. ......... 606/151 | |
| 5,855,614 A | 1/1999 | Stevens et al. | 6,139,540 A | 10/2000 | Rost et al. | |
| 5,868,702 A | 2/1999 | Stevens et al. | 6,143,004 A | 11/2000 | Davis et al. | |
| 5,868,763 A | 2/1999 | Spence et al. | 6,149,658 A | 11/2000 | Gardiner et al. | |
| 5,871,528 A | 2/1999 | Camps et al. | 6,152,935 A | 11/2000 | Kammerer et al. | |
| 5,879,371 A | 3/1999 | Gardiner et al. | 6,152,937 A | 11/2000 | Peterson et al. | |
| 5,881,943 A | 3/1999 | Heck et al. | 6,159,165 A * | 12/2000 | Ferrera et al. ................ 606/191 | |
| 5,882,340 A | 3/1999 | Yoon | 6,159,225 A | 12/2000 | Makower | |
| 5,891,130 A | 4/1999 | Palermo et al. | 6,165,183 A | 12/2000 | Kuehn et al. | |
| 5,891,160 A | 4/1999 | Williamson, IV et al. | 6,165,185 A | 12/2000 | Shennib et al. | |
| 5,893,369 A | 4/1999 | LeMole | 6,171,320 B1 | 1/2001 | Monassevitch | |
| 5,893,865 A | 4/1999 | Swindle et al. | 6,171,321 B1 | 1/2001 | Gifford, III et al. | |
| 5,893,886 A | 4/1999 | Zegdi et al. | 6,176,413 B1 | 1/2001 | Heck et al. | |
| 5,895,394 A | 4/1999 | Kienzle et al. | 6,176,864 B1 | 1/2001 | Chapman | |
| 5,897,565 A * | 4/1999 | Foster ........................ 606/158 | 6,179,840 B1 | 1/2001 | Bowman | |
| 5,904,697 A | 5/1999 | Gifford, III et al. | 6,179,848 B1 | 1/2001 | Solem | |
| 5,908,428 A | 6/1999 | Scirica et al. | 6,179,849 B1 | 1/2001 | Yencho et al. | |
| 5,911,352 A | 6/1999 | Racenet et al. | 6,183,512 B1 | 2/2001 | Howanec et al. | |
| 5,919,207 A | 7/1999 | Taheri | 6,190,373 B1 | 2/2001 | Palermo et al. | |
| 5,931,842 A | 8/1999 | Goldsteen et al. | 6,193,733 B1 | 2/2001 | Adams | |
| 5,941,434 A | 8/1999 | Green | 6,193,734 B1 | 2/2001 | Bolduc et al. | |
| 5,941,442 A | 8/1999 | Geiste et al. | 6,197,037 B1 | 3/2001 | Hair | |
| 5,941,888 A | 8/1999 | Wallace et al. | 6,217,611 B1 | 4/2001 | Klostermeyer | |
| 5,941,908 A | 8/1999 | Goldsteen et al. | 6,221,083 B1 | 4/2001 | Mayer | |
| 5,944,730 A | 8/1999 | Nobles et al. | 6,241,738 B1 | 6/2001 | Dereume | |
| 5,951,576 A | 9/1999 | Wakabayashi | 6,241,741 B1 | 6/2001 | Duhaylongsod et al. | |
| 5,951,600 A | 9/1999 | Lemelson | 6,248,117 B1 | 6/2001 | Blatter | |
| 5,954,735 A | 9/1999 | Rygaard | 6,250,308 B1 | 6/2001 | Cox | |
| 5,957,363 A | 9/1999 | Heck | 6,254,615 B1 | 7/2001 | Bolduc et al. | |
| 5,957,938 A | 9/1999 | Zhu et al. | 6,269,819 B1 * | 8/2001 | Oz et al. ..................... 128/898 | |
| 5,957,940 A * | 9/1999 | Tanner et al. ................ 606/155 | 6,280,460 B1 | 8/2001 | Bolduc et al. | |
| 5,961,481 A | 10/1999 | Sterman et al. | 6,283,979 B1 | 9/2001 | Mers Kelly et al. | |
| 5,961,539 A | 10/1999 | Northrup, III et al. | 6,283,993 B1 | 9/2001 | Cosgrove et al. | |
| 5,964,772 A | 10/1999 | Bolduc et al. | 6,296,622 B1 | 10/2001 | Kurz et al. | |
| 5,964,782 A | 10/1999 | Lafontaine et al. | 6,296,656 B1 | 10/2001 | Bolduc et al. | |
| 5,972,024 A * | 10/1999 | Northrup et al. ............. 606/232 | 6,306,141 B1 | 10/2001 | Jervis | |
| 5,976,159 A | 11/1999 | Bolduc et al. | 6,332,893 B1 | 12/2001 | Mortier et al. | |
| 5,976,161 A | 11/1999 | Kirsch et al. | 6,346,074 B1 | 2/2002 | Roth | |
| 5,976,164 A | 11/1999 | Bencini et al. | 6,346,112 B2 | 2/2002 | Adams | |
| 5,976,178 A | 11/1999 | Goldsteen et al. | 6,350,269 B1 | 2/2002 | Shipp et al. | |
| 5,984,917 A | 11/1999 | Fleischman et al. | 6,352,543 B1 | 3/2002 | Cole | |
| 5,984,959 A | 11/1999 | Robertson et al. | 6,358,258 B1 | 3/2002 | Arcia et al. | |
| 5,989,242 A | 11/1999 | Saadat et al. | 6,361,559 B1 | 3/2002 | Houser et al. | |

| | | |
|---|---|---|
| 6,368,348 B1 | 4/2002 | Gabbay |
| 6,371,964 B1 | 4/2002 | Vargas et al. |
| 6,387,105 B1 | 5/2002 | Gifford, III et al. |
| 6,391,038 B2 | 5/2002 | Vargas et al. |
| 6,402,764 B1 | 6/2002 | Hendricksen et al. |
| 6,406,492 B1 | 6/2002 | Lytle |
| 6,406,493 B1 | 6/2002 | Tu et al. |
| 6,409,739 B1 | 6/2002 | Nobles et al. |
| 6,409,758 B2 | 6/2002 | Stobie et al. |
| 6,416,527 B1 | 7/2002 | Berg et al. |
| 6,418,597 B1 | 7/2002 | Deschenes et al. |
| 6,419,658 B1 | 7/2002 | Restelli et al. |
| 6,419,681 B1 | 7/2002 | Vargas et al. |
| 6,419,695 B1 | 7/2002 | Gabbay |
| 6,425,900 B1 | 7/2002 | Knodel et al. |
| 6,428,550 B1 | 8/2002 | Vargas et al. |
| 6,428,555 B1 | 8/2002 | Koster, Jr. |
| 6,451,048 B1 | 9/2002 | Berg et al. |
| 6,461,320 B1 | 10/2002 | Yencho et al. |
| 6,475,222 B1 | 11/2002 | Berg et al. |
| 6,478,804 B2 | 11/2002 | Vargas et al. |
| 6,485,496 B1 | 11/2002 | Suyker et al. |
| 6,491,707 B2 | 12/2002 | Makower et al. |
| 6,497,671 B2 | 12/2002 | Ferrera et al. |
| 6,497,710 B2 | 12/2002 | Yencho et al. |
| 6,514,265 B2 | 2/2003 | Ho et al. |
| 6,517,558 B2 | 2/2003 | Gittings et al. |
| 6,524,338 B1 | 2/2003 | Gundry |
| 6,533,812 B2 | 3/2003 | Swanson et al. |
| 6,537,288 B2 | 3/2003 | Vargas et al. |
| 6,547,799 B2 | 4/2003 | Hess et al. |
| 6,551,332 B1 * | 4/2003 | Nguyen et al. ............ 606/151 |
| 6,562,053 B2 | 5/2003 | Schulze et al. |
| 6,575,985 B2 | 6/2003 | Knight et al. |
| 6,589,255 B2 | 7/2003 | Schulze et al. |
| 6,607,541 B1 | 8/2003 | Gardiner et al. |
| 6,607,542 B1 | 8/2003 | Wild et al. |
| 6,613,059 B2 | 9/2003 | Schaller et al. |
| 6,629,988 B2 | 10/2003 | Weadock |
| 6,635,214 B2 | 10/2003 | Rapacki et al. |
| 6,641,593 B1 * | 11/2003 | Schaller et al. ............ 606/157 |
| 6,648,900 B2 | 11/2003 | Fleischman et al. |
| 6,651,670 B2 | 11/2003 | Rapacki et al. |
| 6,651,672 B2 | 11/2003 | Roth |
| 6,652,540 B1 | 11/2003 | Cole et al. |
| 6,652,541 B1 | 11/2003 | Vargas et al. |
| 6,660,015 B1 | 12/2003 | Berg et al. |
| 6,682,540 B1 | 1/2004 | Sancoff et al. |
| 6,695,859 B1 | 2/2004 | Golden et al. |
| 6,702,826 B2 | 3/2004 | Liddicoat et al. |
| 6,709,442 B2 | 3/2004 | Miller et al. |
| 6,712,829 B2 | 3/2004 | Schulze |
| 6,719,768 B1 | 4/2004 | Cole et al. |
| 6,743,243 B1 | 6/2004 | Roy et al. |
| 6,749,622 B2 | 6/2004 | McGuckin et al. |
| 6,776,782 B2 | 8/2004 | Schulze |
| 6,776,784 B2 | 8/2004 | Ginn |
| 6,776,785 B1 | 8/2004 | Yencho et al. |
| 6,802,847 B1 | 10/2004 | Carson et al. |
| 6,821,286 B1 | 11/2004 | Carranza et al. |
| 6,869,444 B2 | 3/2005 | Gabbay |
| 6,913,607 B2 | 7/2005 | Ainsworth et al. |
| 6,918,917 B1 * | 7/2005 | Nguyen et al. ............ 606/139 |
| 6,921,407 B2 * | 7/2005 | Nguyen et al. ............ 606/142 |
| 6,926,730 B1 * | 8/2005 | Nguyen et al. ............ 606/213 |
| 6,945,980 B2 | 9/2005 | Nguyen et al. |
| 6,955,679 B1 | 10/2005 | Hendricksen et al. |
| 6,960,221 B2 | 11/2005 | Ho et al. |
| 6,979,337 B2 | 12/2005 | Kato |
| 6,979,338 B1 | 12/2005 | Loshakove et al. |
| 7,022,131 B1 | 4/2006 | Derowe et al. |
| 7,056,330 B2 | 6/2006 | Gayton |
| 7,063,711 B1 | 6/2006 | Loshakove et al. |
| 7,070,618 B2 | 7/2006 | Streeter |
| 7,182,769 B2 | 2/2007 | Ainsworth et al. |
| 7,220,268 B2 | 5/2007 | Blatter |
| 2001/0018592 A1 * | 8/2001 | Schaller et al. ............ 606/151 |
| 2001/0018593 A1 | 8/2001 | Nguyen et al. |
| 2001/0018611 A1 | 8/2001 | Solem et al. |
| 2001/0021856 A1 | 9/2001 | Bolduc et al. |
| 2001/0047181 A1 | 11/2001 | Ho et al. |
| 2002/0010490 A1 | 1/2002 | Schaller et al. |
| 2002/0042623 A1 | 4/2002 | Blatter et al. |
| 2002/0082614 A1 | 6/2002 | Logan et al. |
| 2002/0099395 A1 | 7/2002 | Acampora et al. |
| 2002/0151916 A1 | 10/2002 | Muramatsu et al. |
| 2002/0165561 A1 | 11/2002 | Ainsworth et al. |
| 2002/0173803 A1 | 11/2002 | Yang et al. |
| 2003/0074012 A1 | 4/2003 | Nguyen et al. |
| 2003/0078603 A1 * | 4/2003 | Schaller et al. ............ 606/151 |
| 2003/0083742 A1 | 5/2003 | Spence et al. |
| 2003/0093118 A1 | 5/2003 | Ho et al. |
| 2003/0125755 A1 * | 7/2003 | Schaller et al. ............ 606/151 |
| 2003/0191481 A1 * | 10/2003 | Nguyen et al. ............ 606/151 |
| 2003/0195531 A1 * | 10/2003 | Gardiner et al. ............ 606/151 |
| 2003/0199974 A1 * | 10/2003 | Lee et al. ................ 623/2.36 |
| 2004/0050393 A1 | 3/2004 | Golden et al. |
| 2004/0068276 A1 | 4/2004 | Golden et al. |
| 2004/0102797 A1 * | 5/2004 | Golden et al. ............ 606/153 |
| 2004/0111099 A1 * | 6/2004 | Nguyen et al. ............ 606/139 |
| 2004/0138685 A1 | 7/2004 | Clague et al. |
| 2004/0176663 A1 | 9/2004 | Edoga |
| 2004/0193259 A1 | 9/2004 | Gabbay |
| 2005/0004582 A1 | 1/2005 | Edoga |
| 2005/0021054 A1 * | 1/2005 | Ainsworth et al. ......... 606/143 |
| 2005/0043749 A1 | 2/2005 | Breton et al. |
| 2005/0065601 A1 | 3/2005 | Lee et al. |
| 2005/0070924 A1 | 3/2005 | Schaller et al. |
| 2005/0075659 A1 | 4/2005 | Realyvasquez et al. |
| 2005/0075667 A1 * | 4/2005 | Schaller et al. ............ 606/228 |
| 2005/0080454 A1 | 4/2005 | Drews |
| 2005/0101975 A1 * | 5/2005 | Nguyen et al. ............ 606/151 |
| 2005/0107871 A1 | 5/2005 | Realyvasquez et al. |
| 2005/0131429 A1 | 6/2005 | Ho et al. |
| 2005/0267572 A1 | 12/2005 | Schoon et al. |
| 2006/0004389 A1 * | 1/2006 | Nguyen et al. ............ 606/151 |
| 2006/0253143 A1 | 11/2006 | Edoga |
| 2006/0271081 A1 | 11/2006 | Realyvasquez |
| 2006/0293701 A1 | 12/2006 | Ainsworth et al. |
| 2007/0010835 A1 | 1/2007 | Breton et al. |
| 2007/0027461 A1 | 2/2007 | Gardiner et al. |
| 2007/0106313 A1 | 5/2007 | Golden et al. |
| 2007/0142848 A1 | 6/2007 | Ainsworth et al. |

FOREIGN PATENT DOCUMENTS

| | | |
|---|---|---|
| DE | 0377052 | 6/1923 |
| DE | 27 03 529 | 8/1978 |
| DE | 32 03 410 | 5/1981 |
| DE | 32 27 984 | 2/1984 |
| DE | 3504202 | 8/1985 |
| DE | 41 33 800 | 1/1993 |
| DE | 44 02 058 | 4/1995 |
| DE | 195 47 617 | 9/1997 |
| DE | 19732234 | 1/1999 |
| EP | 0072232 | 2/1983 |
| EP | 0122046 | 3/1983 |
| EP | 0 121 362 | 10/1984 |
| EP | 0129441 | 12/1984 |
| EP | 0130037 | 1/1985 |
| EP | 0140557 | 5/1985 |
| EP | 0 326 426 | 8/1989 |
| EP | 0409569 | 1/1991 |
| EP | 0 432 692 | 6/1991 |
| EP | 0 478 949 | 4/1992 |
| EP | 0 494 636 | 7/1992 |

| | | |
|---|---|---|
| EP | 0 559 429 | 9/1993 |
| EP | 0598529 | 5/1994 |
| EP | 0 419 597 | 12/1994 |
| EP | 0632999 | 1/1995 |
| EP | 0 641 546 | 3/1995 |
| EP | 0656191 | 6/1995 |
| EP | 0687446 | 12/1995 |
| EP | 0705568 | 4/1996 |
| EP | 0 711 532 | 5/1996 |
| EP | 0 734 697 | 10/1996 |
| EP | 0705569 | 10/1996 |
| EP | 0 537 955 | 12/1996 |
| EP | 0 778 005 | 6/1997 |
| EP | 0 815 795 | 1/1998 |
| GB | 2 223 410 | 4/1990 |
| JP | 07308322 | 11/1995 |
| JP | 08336544 | 12/1996 |
| JP | 10-337291 | 12/1998 |
| RU | 2110222 | 5/1998 |
| SU | 577022 | 10/1977 |
| SU | 1186199 | 10/1985 |
| SU | 1456109 | 2/1989 |
| SU | 1560133 | 4/1990 |
| WO | 90/06725 | 6/1990 |
| WO | 90/09149 | 8/1990 |
| WO | 90/14795 | 12/1990 |
| WO | 91/07916 | 6/1991 |
| WO | 91/08708 | 6/1991 |
| WO | 91/17712 | 11/1991 |
| WO | 92/05828 | 4/1992 |
| WO | 92/12676 | 8/1992 |
| WO | 92/22041 | 12/1992 |
| WO | 93/01750 | 2/1993 |
| WO | 93/20756 | 10/1993 |
| WO | 94/15535 | 7/1994 |
| WO | 94/15537 | 7/1994 |
| WO | 96/00035 | 1/1996 |
| WO | 96/06565 | 3/1996 |
| WO | 96/38090 | 12/1996 |
| WO | 97/12555 | 4/1997 |
| WO | 97/16122 | 5/1997 |
| WO | 97/27898 | 8/1997 |
| WO | 97/28744 | 8/1997 |
| WO | 97/31575 | 9/1997 |
| WO | 97/32526 | 9/1997 |
| WO | 97/40754 | 11/1997 |
| WO | 97/42881 | 11/1997 |
| WO | 98/19636 | 5/1998 |
| WO | 98/30153 | 7/1998 |
| WO | 98/42262 | 10/1998 |
| WO | 98/48707 | 11/1998 |
| WO | 98/52475 | 11/1998 |
| WO | 99/07294 | 2/1999 |
| WO | 99/12484 | 3/1999 |
| WO | 99/15088 | 4/1999 |
| WO | 99/37218 | 7/1999 |
| WO | 99/62406 | 12/1999 |
| WO | 99/62408 | 12/1999 |
| WO | 99/62409 | 12/1999 |
| WO | 99/62415 | 12/1999 |
| WO | 99/63910 | 12/1999 |
| WO | 99/65409 | 12/1999 |
| WO | 00/03759 | 1/2000 |
| WO | 00/15144 | 3/2000 |
| WO | 00/59380 | 10/2000 |
| WO | 00/60995 | 10/2000 |
| WO | 00/64381 | 11/2000 |
| WO | 00/74603 | 12/2000 |
| WO | 01/19292 | 3/2001 |
| WO | 01/26557 | 4/2001 |
| WO | 01/26586 | 4/2001 |
| WO | 01/28432 | 4/2001 |
| WO | 01/54618 | 8/2001 |
| WO | 01/74254 | 10/2001 |
| WO | 02/13701 | 2/2002 |
| WO | 02/13702 | 2/2002 |
| WO | 02/30295 | 4/2002 |
| WO | 02/30298 | 4/2002 |
| WO | 02/34143 | 5/2002 |
| WO | 02/080779 | 10/2002 |
| WO | 02/080780 | 10/2002 |
| WO | 02/087425 | 11/2002 |
| WO | 03/053289 | 7/2003 |
| WO | 03/088875 | 10/2003 |
| WO | 2005/011468 | 2/2005 |
| WO | 2005/058170 | 6/2005 |

OTHER PUBLICATIONS

Wylie et al., Edwin J., Manual of Vascular Surgery (Springer-Verlag New York), (1980) Table of contents only.
International Search Report PCT/US99/12563.
Written Opinion PCT/US99/12563 dated Jun. 12, 2000.
"VCS Clip Applier System," published in 1995 by Auto Suture Company, a Division of U.S. Surgical Corporation.
Chitwood Jr., Mitral Valve Repair: Ischemic, Mastery of Cardiothoracic Surgery, Lippencott-Raven Publishers, 1998, Chapter 32, pp. 309-321.
Grondin, et al., Carpentier's Annulus and De Vega's Annuloplasty: The end of the tricuspid challenge, Nov. 1975, vol. 70, pp. 852-861.
Holper, et al., Surgery For Tricuspid Insufficiency: Long Term Follow-Up After De Vega Annuloplasty, Thorac Cardiovasc Surgeon, 41, 1993.
Maisano, et al., The Double Orifice Technique as a Standardized Approach to Treat Mitral Regurgitation Due to Severe Myxomatous Disease: Surgical Technique, European Journal of Cardiothoracic Surgery, vol. 17, 2000, 201-205.
Rabago, et al., The New De Vega Technique In Tricuspid Annuloplasty: Results in 150 patients, J. Cardiovas Surg. 1980, 21 pp. 231-238.
Rivera, et al., Carpentier's Flexible Ring Versus De Vega's Annuloplasty, J Thorac Cardiovas Surg, Feb. 1985, 89 pp. 196-203.
Wei, et al., De Vega's Semicircular Annuloplasty for Tricuspid Valve Regurgitation, Ann Thorac Surg, 1993, 55: pp. 482-485.
Wylie, et al., Manual of Vascular Surgery, R. H. Egdahl ed. Spring-Verlag: New York, vol. II, 1986, Table of Contents only.
Wylie, et al., Manual of Vascular Surgery, Springer-Verlag New York, vol. I, 1980, Table of Contents only.
Yun, et al. Mitral Valve Replacement, Mastery of Cardiothoracic Surgery, Lippencott-Raven Publishers, 1998, Chapter 34, pp. 329-341.
International Search Report PCT/US98/00462.
International Search Report PCT/US98/00795.
International Search Report PCT/US98/14211.
International Search Report PCT/US99/12563.
International Search Report PCT/US99/12566.
International Search Report PCT/US00/09092.
International Search Report PCT/US01/10501.
International Search Report PCT/US01/31709.
International Search Report PCT/US01/42653.
International Search Report PCT/US02/10865.
International Search Report PCT/US02/10866.
International Search Report PCT/US02/14261.
International Search Report PCT/US03/12073.
International Preliminary Examination Report PCT/US98/00462.
International Preliminary Examination Report PCT/US98/00795.
International Preliminary Examination Report PCT/US99/12566.
International Preliminary Examination Report PCT/US00/09092.
International Preliminary Examination Report PCT/US01/31709.
International Preliminary Examination Report PCT/US01/42653.
International Preliminary Examination Report PCT/US02/14261.
International Preliminary Examination Report PCT/US02/10865.
International Preliminary Examination Report PCT/US02/10866.
International Preliminary Examination Report PCT/US03/12073.
Written Opinion PCT/US99/12563.
Written Opinion PCT/US99/12566.

Written Opinion PCT/US00/09092.
Written Opinion PCT/US01/10501.
Written Opinion PCT/US01/31709.
Written Opinion PCT/US02/10866.
Written Opinion PCT/US02/14261.
Written Opinion PCT/US03/12073.

International Preliminary Report On Patentability PCT/US2004/023728.
EPO Search Report mailed Nov. 3, 2008 (6 pgs.).
US 6,503,260, 01/2003, Schaller et al. (withdrawn)

\* cited by examiner

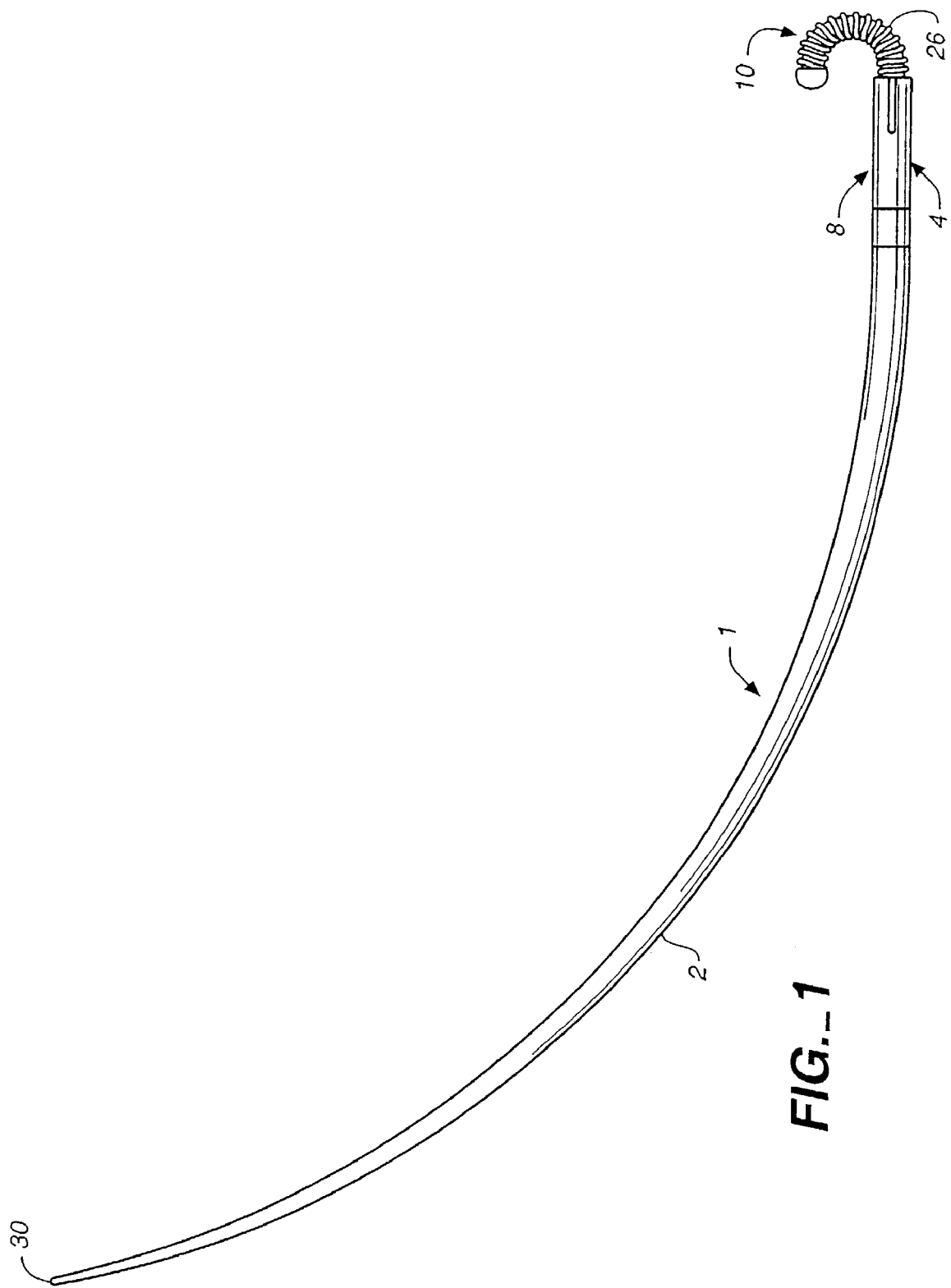

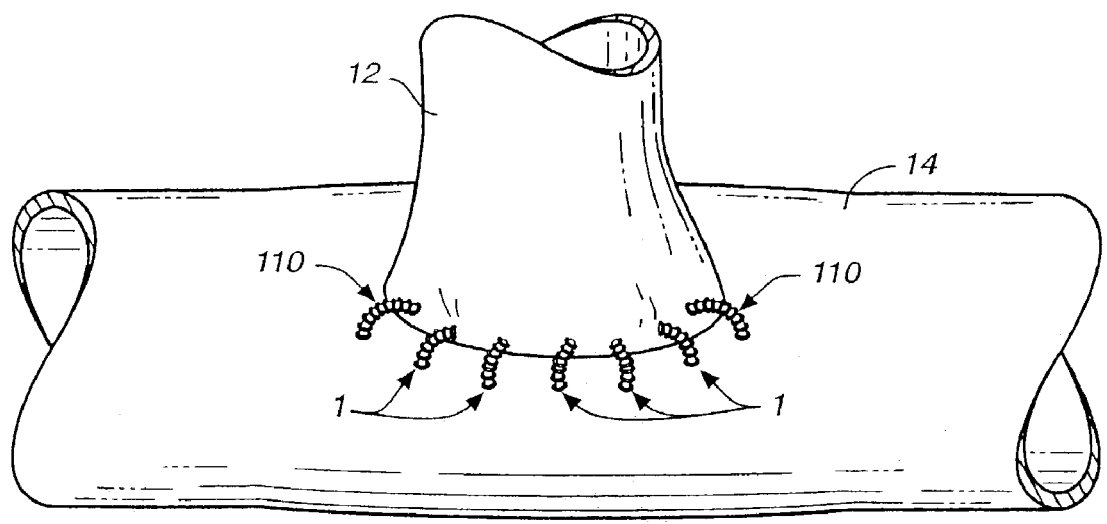
FIG._2A
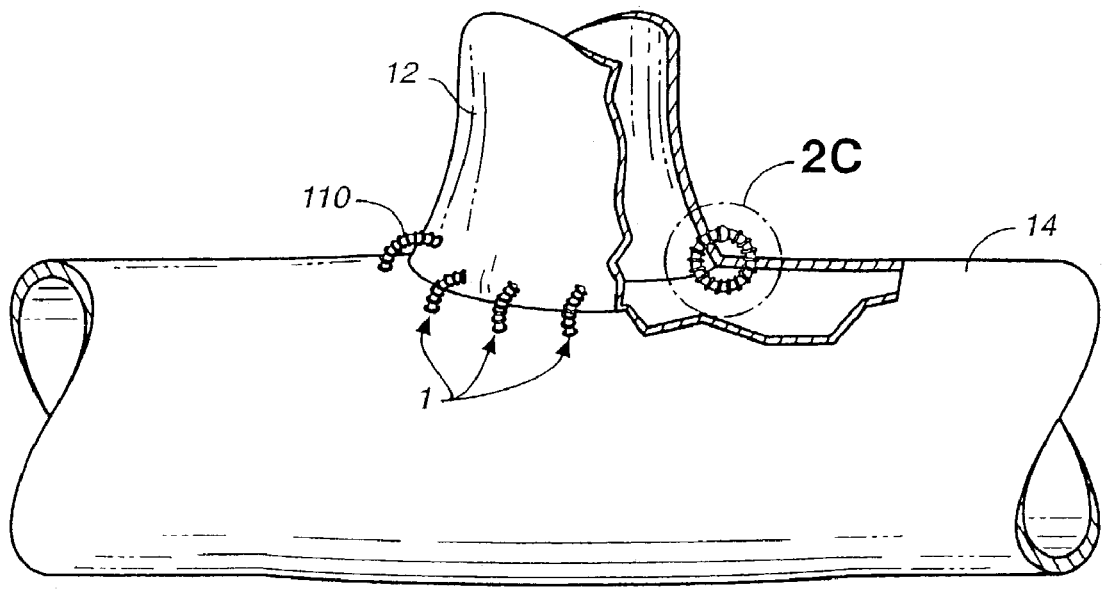
FIG._2B

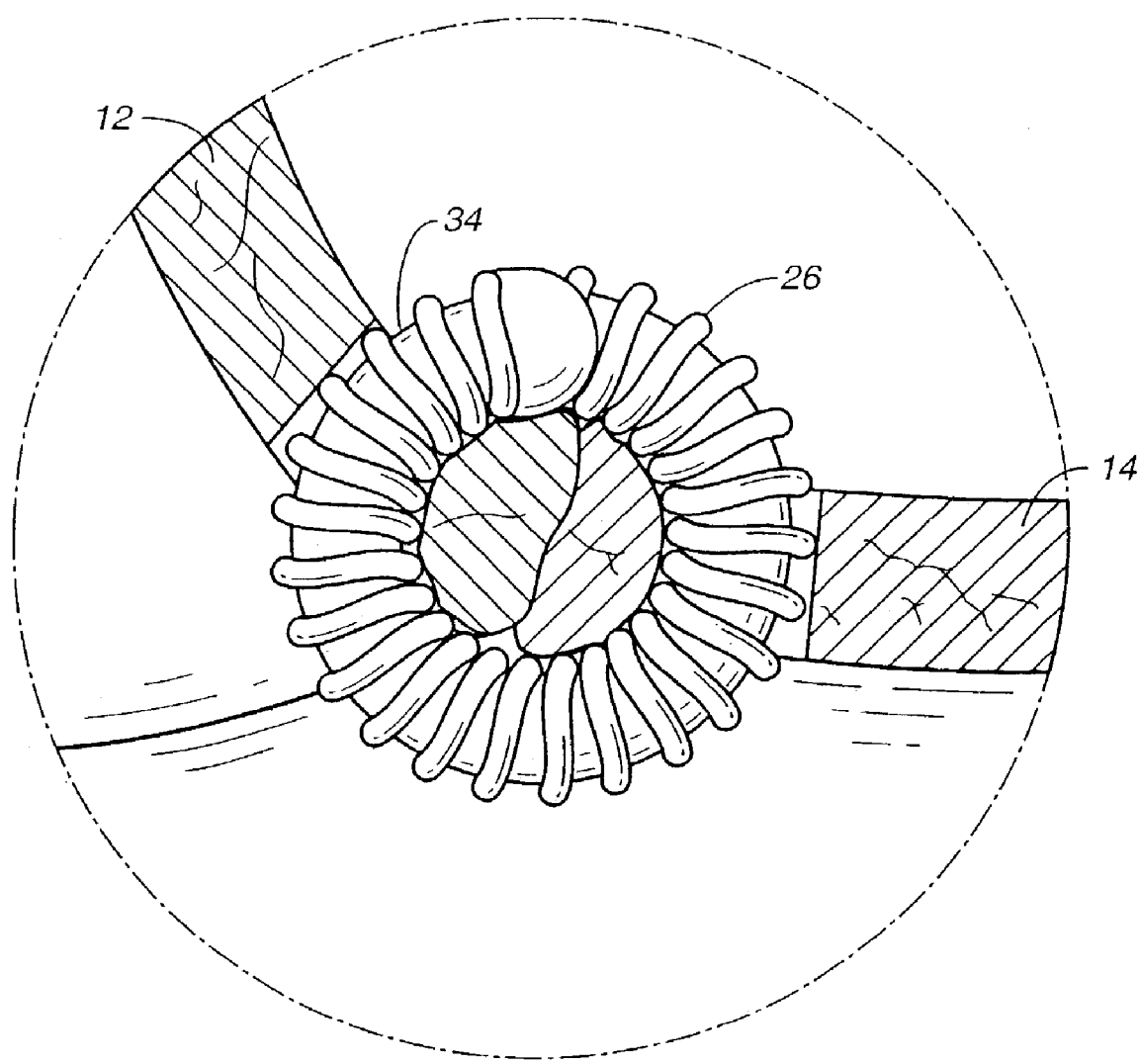
FIG._2C

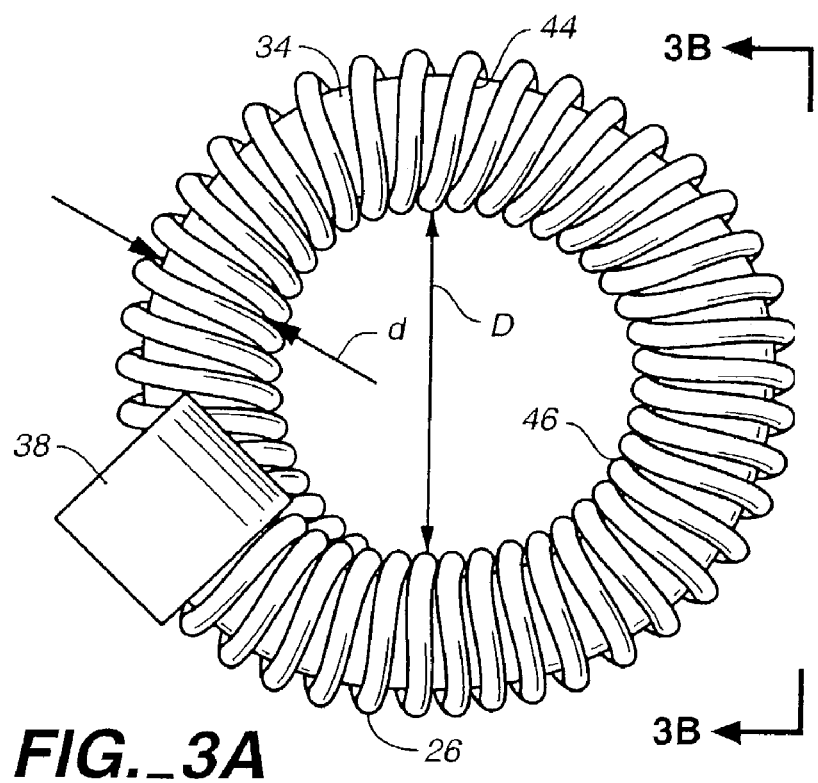
FIG._3A
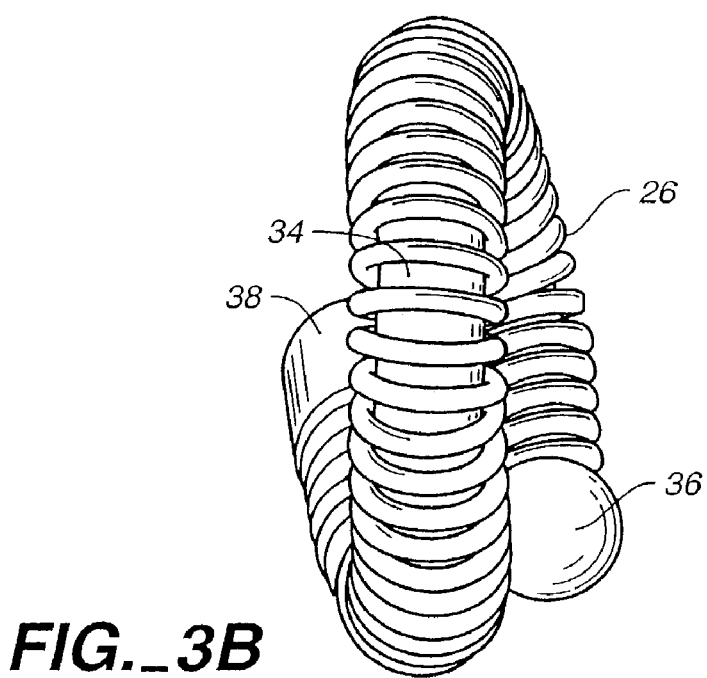
FIG._3B

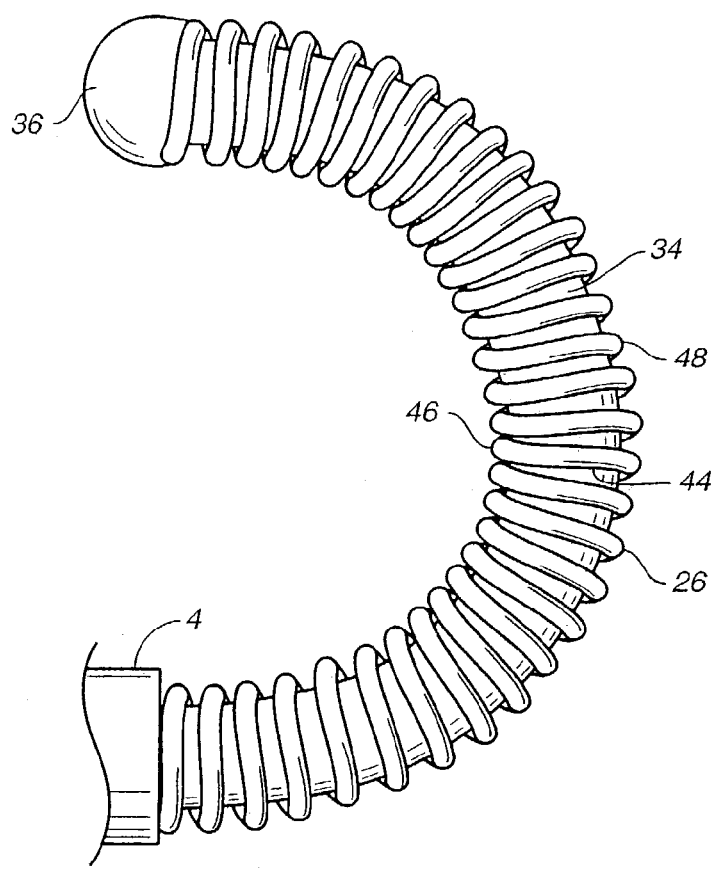
FIG._3C
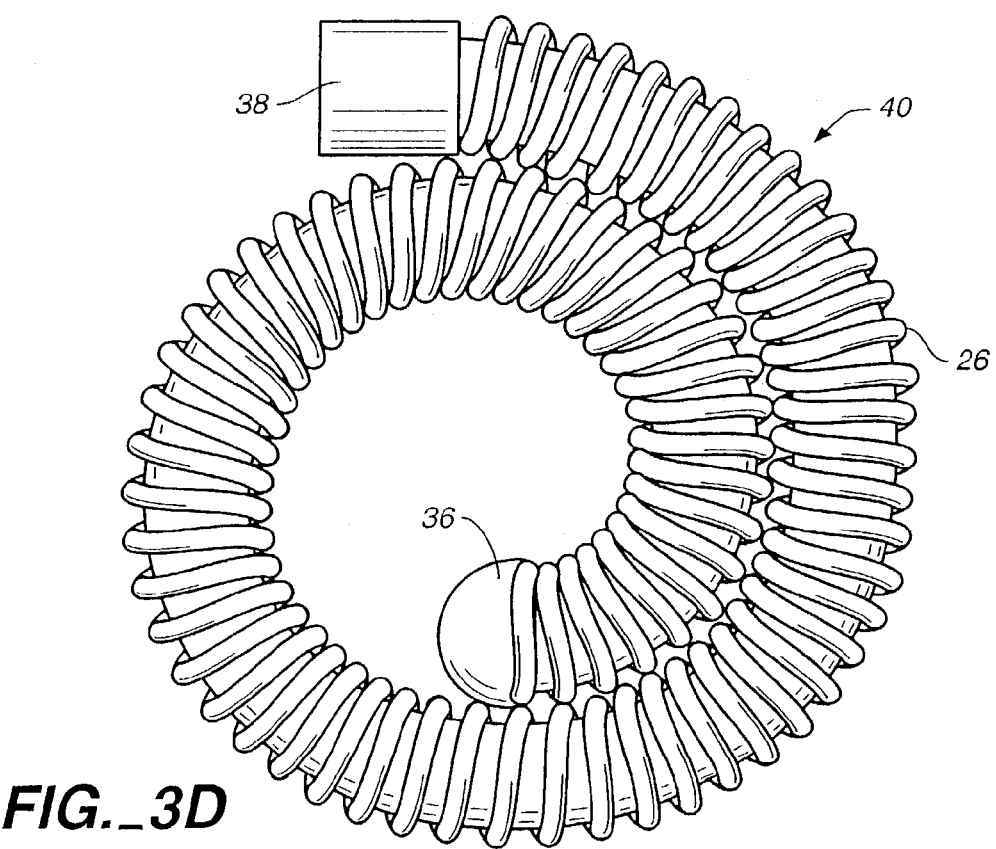
FIG._3D

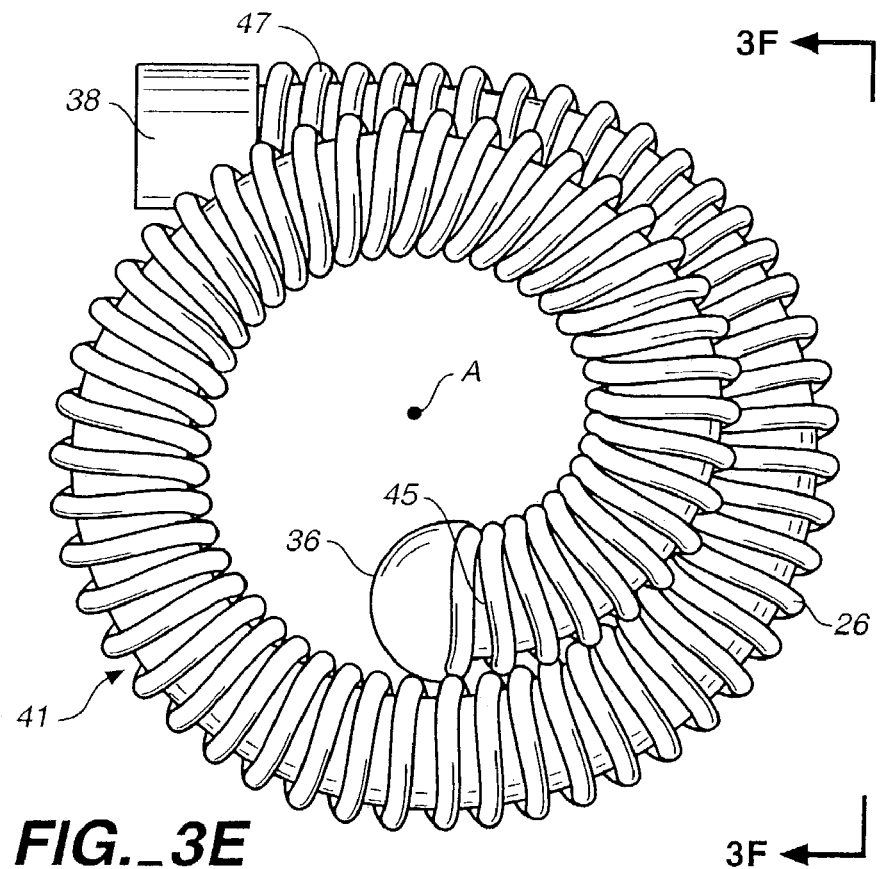
FIG._3E
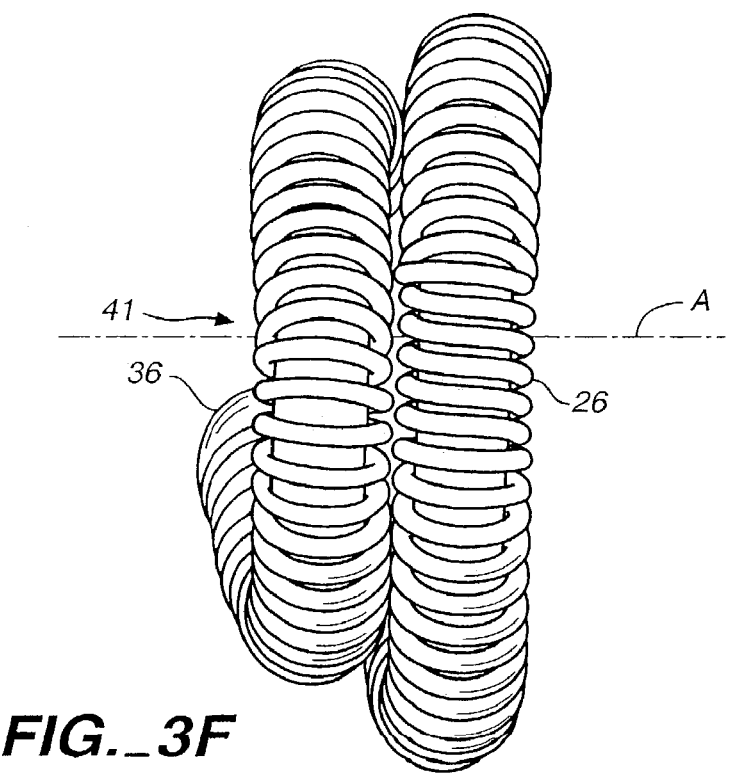
FIG._3F

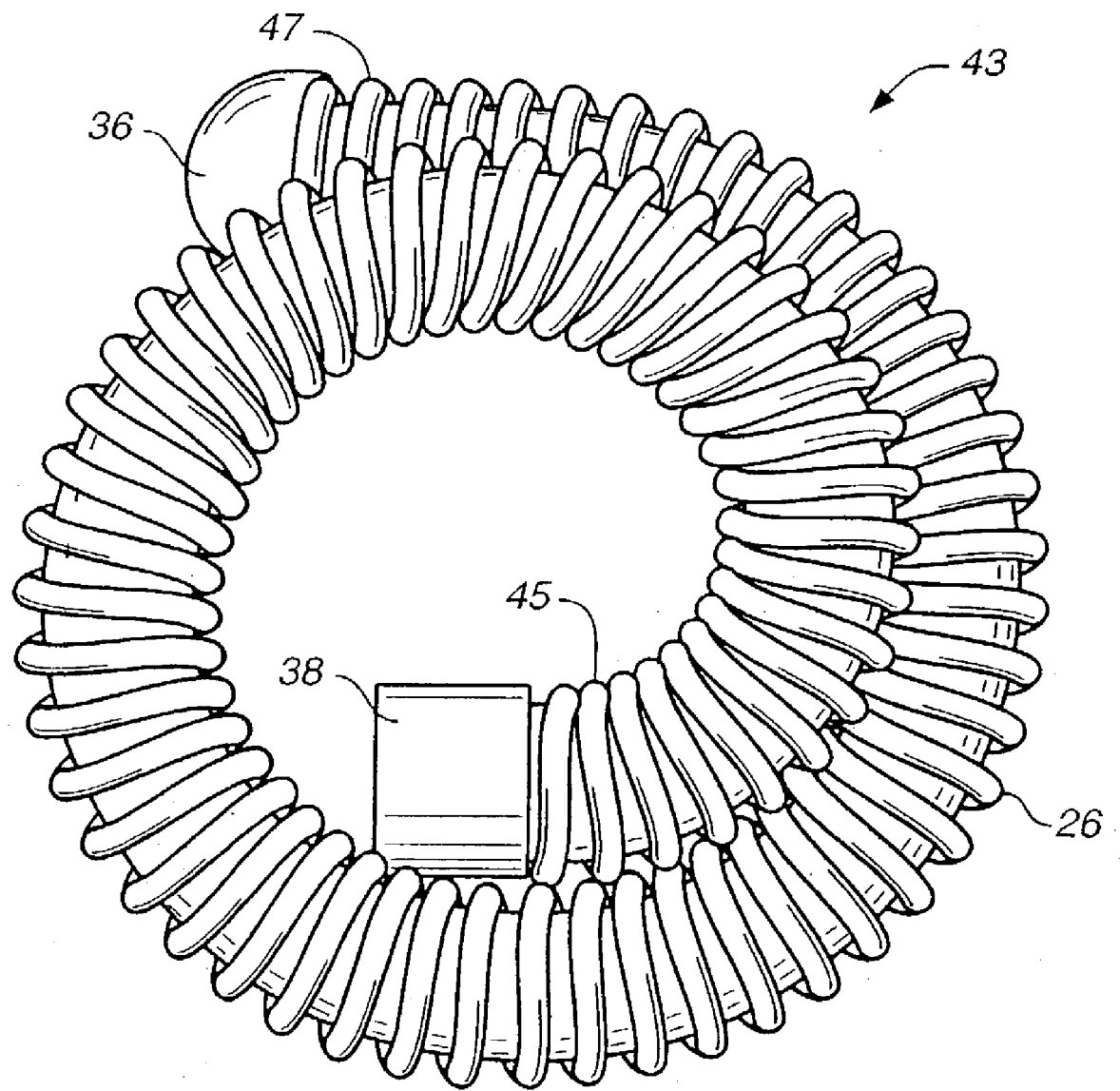
FIG._3G

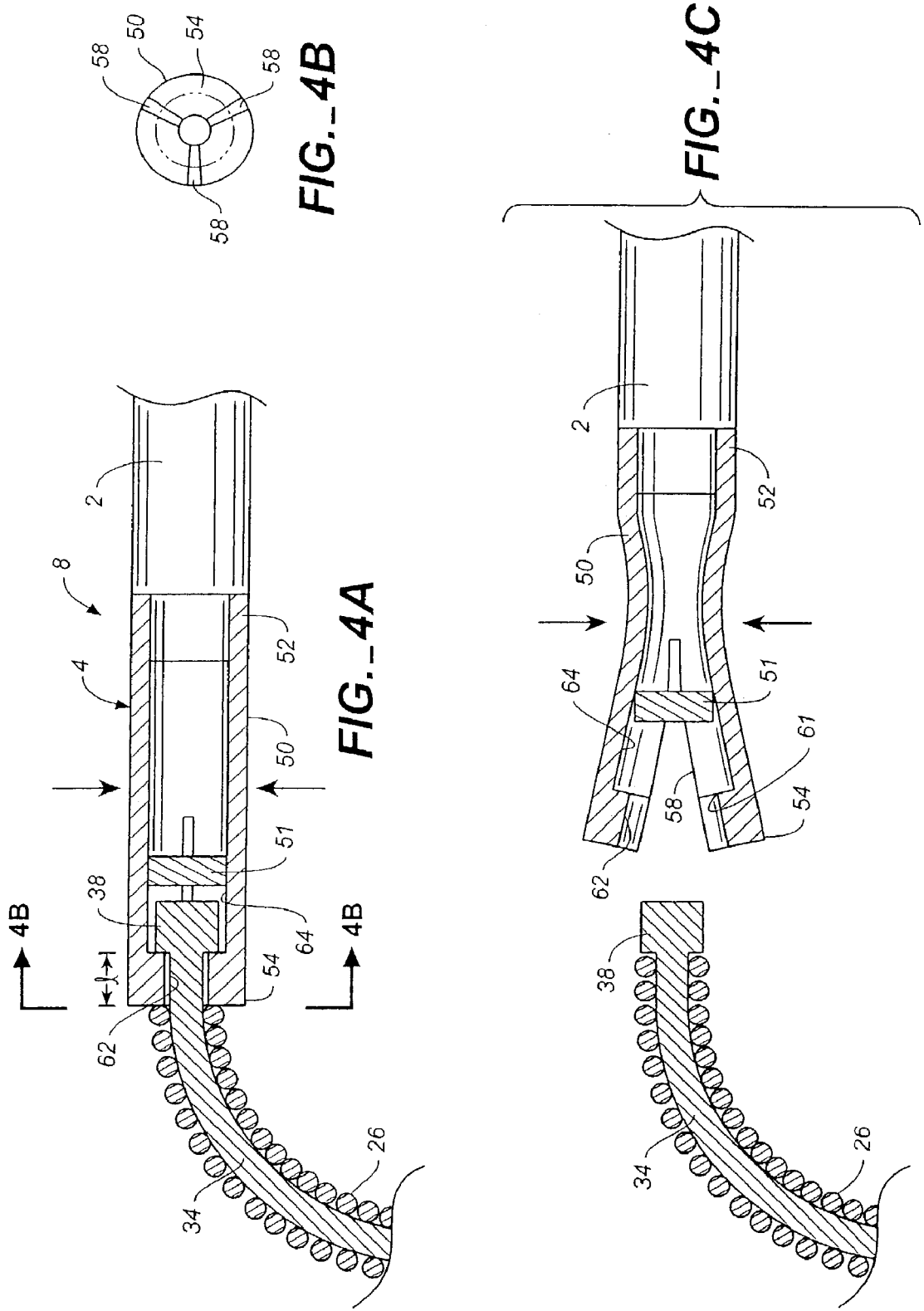

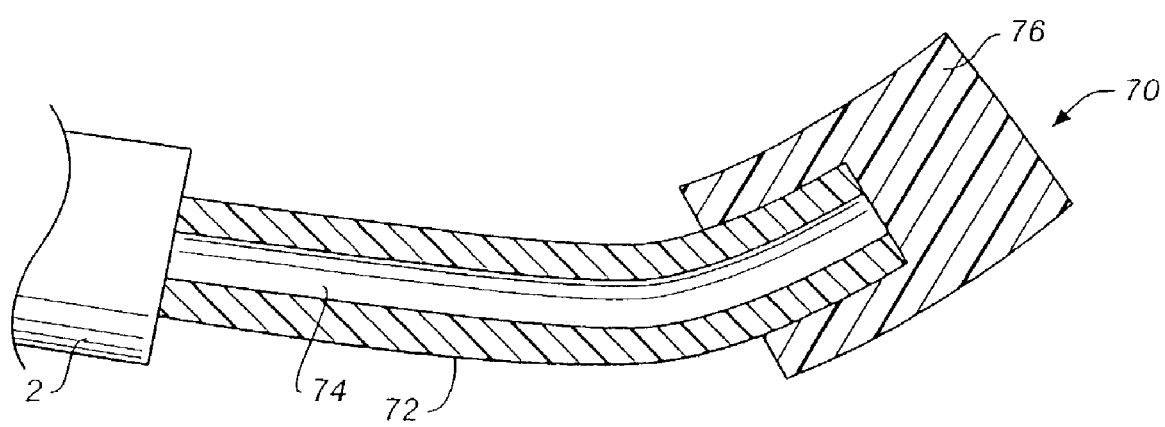
FIG._5

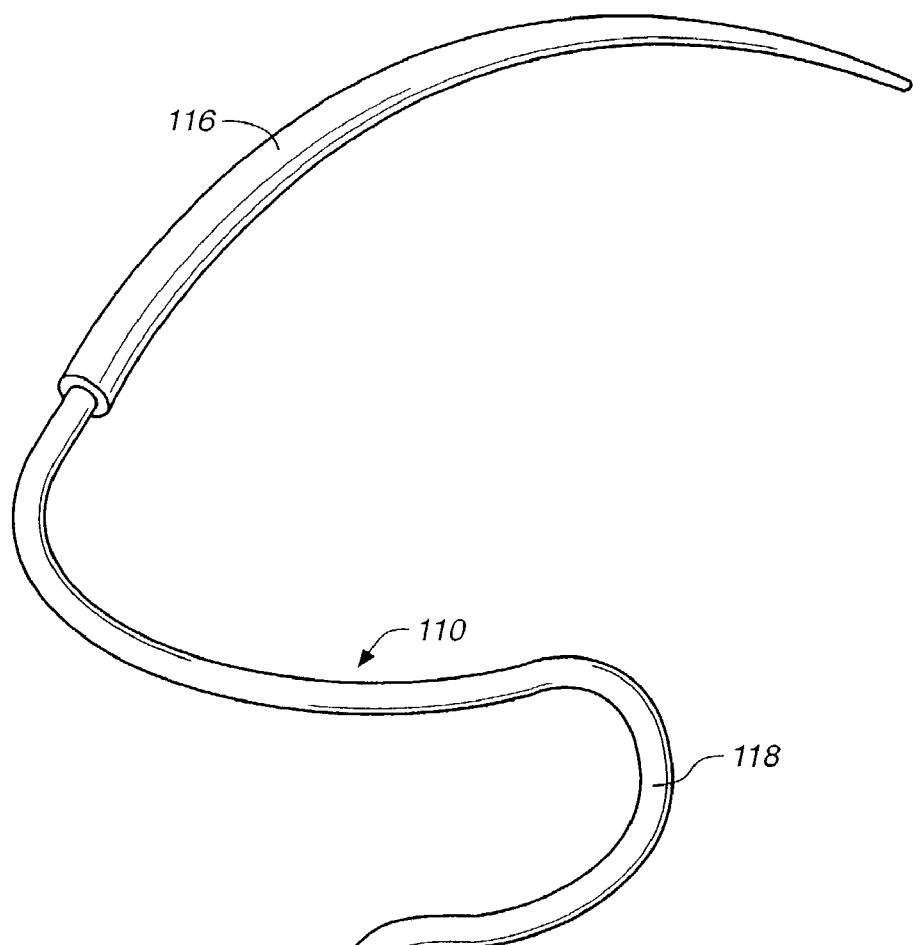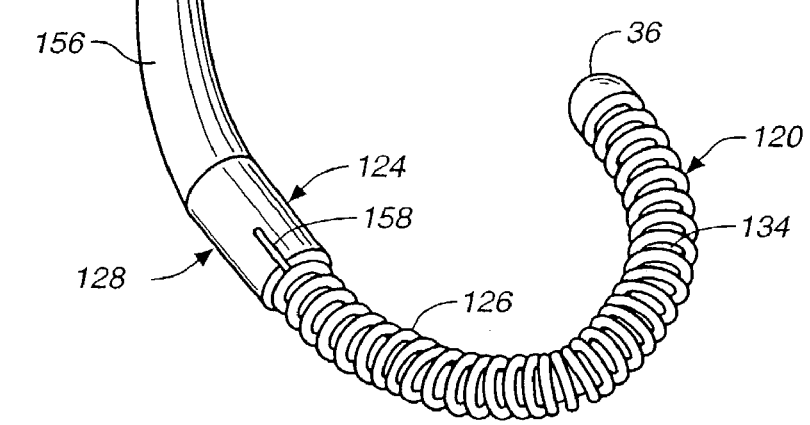
FIG._6

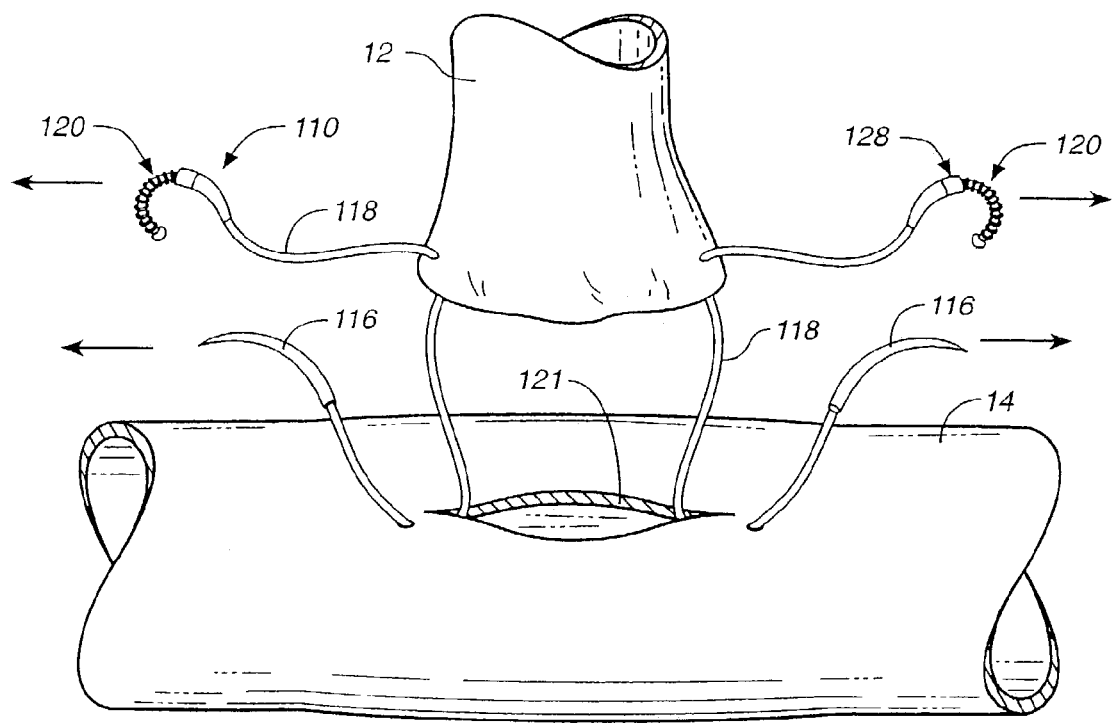
FIG._7
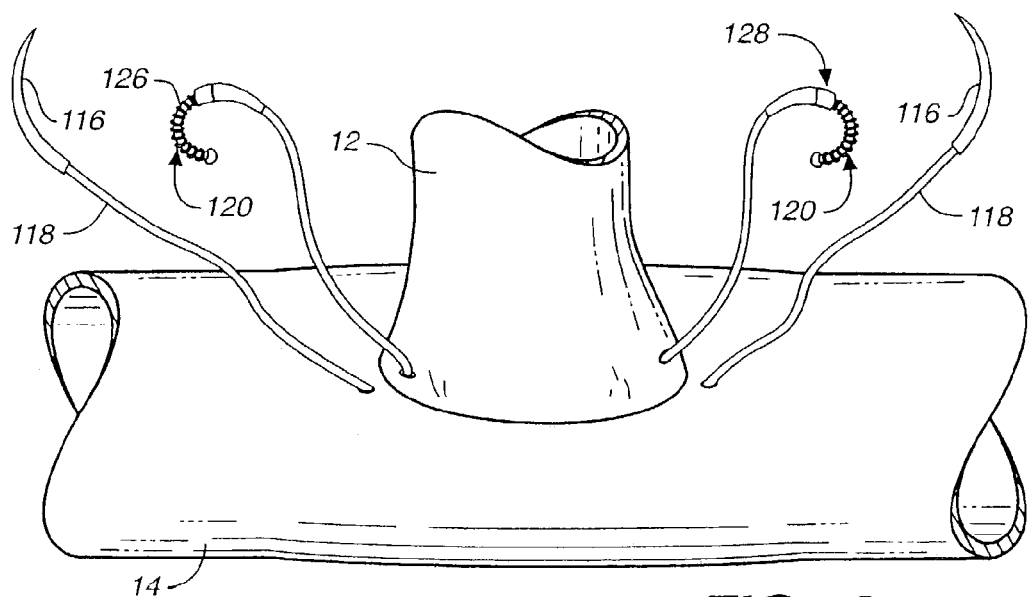
FIG._8

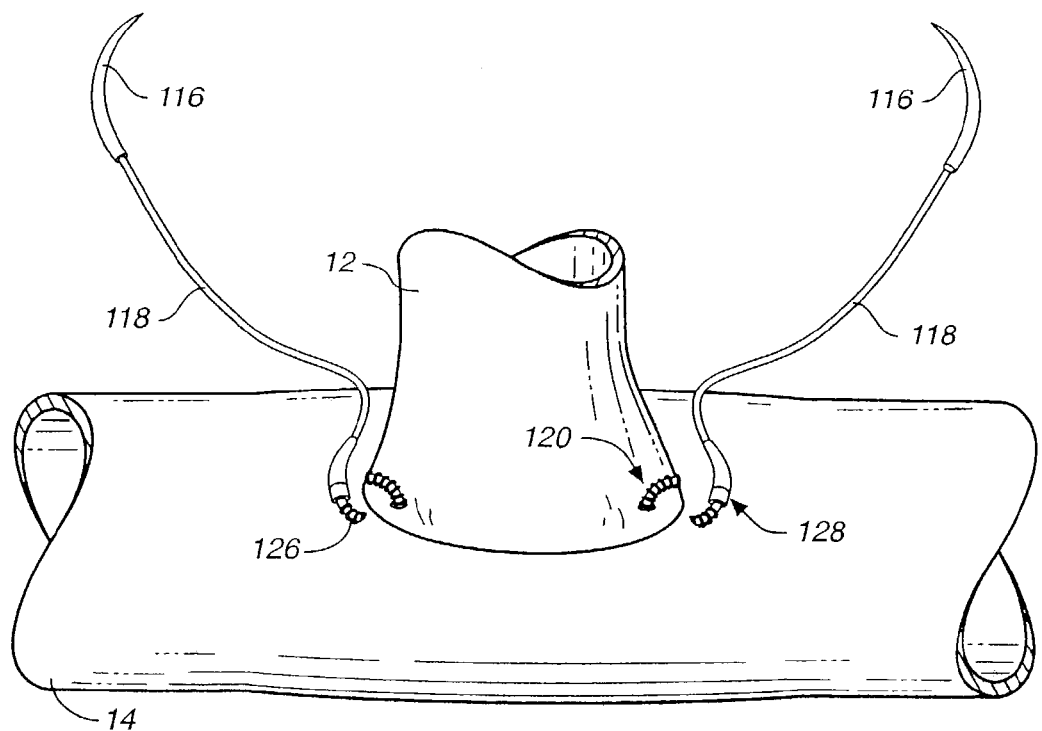
FIG._9
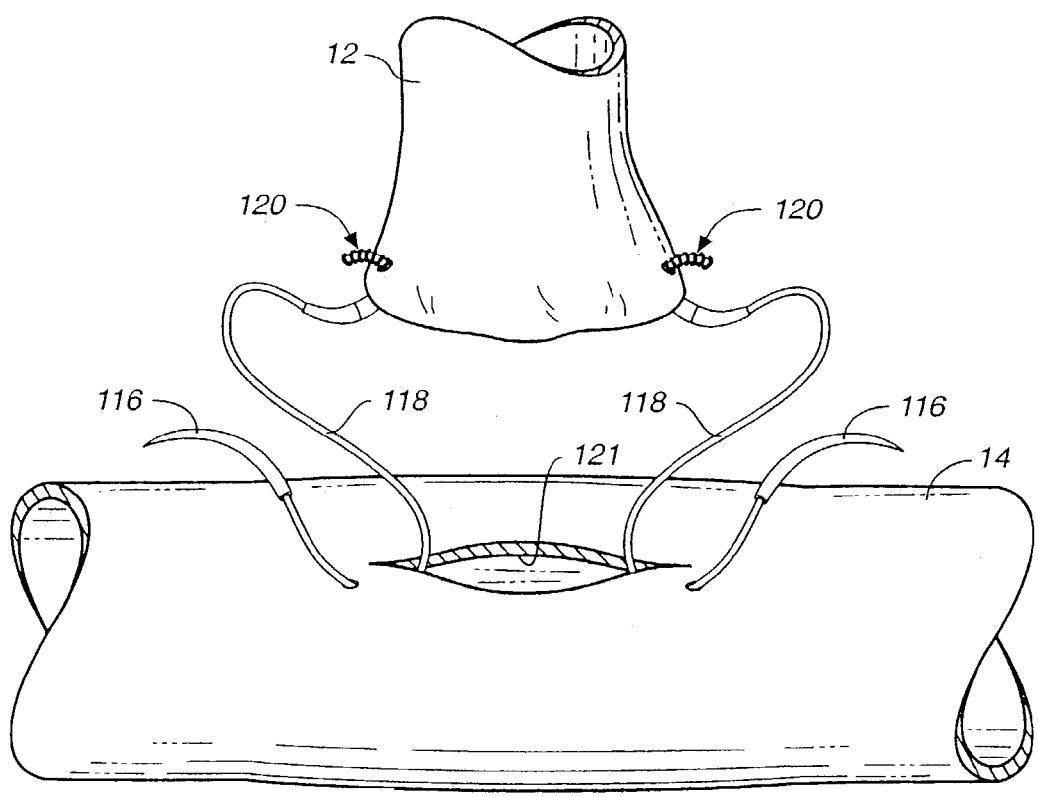
FIG._10

TISSUE CONNECTOR APPARATUS AND METHODS

CROSS-REFERENCE TO RELATED APPLICATIONS

This application is a continuation of U.S. patent application Ser. No. 09/090,305, entitled Tissue Connector Apparatus and Methods and filed Jun. 3, 1998, now U.S. Pat. No. 6,641,593, which application is incorporated by reference in its entirety and to which priority is claimed under 35 U.S.C. §120.

FIELD OF THE INVENTION

The present invention relates to instruments and methods for connecting body tissues, or body tissue to prostheses.

BACKGROUND OF THE INVENTION

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trocar, which is a pointed, piercing device, is delivered into the body with a cannula. After the trocar pierces the abdominal or thoracic wall, it is removed and the cannula is left with one end in the body cavity, where the operation is to take place, and the other end opening to the outside. A cannula has a small inside diameter, typically 5-10 millimeters, and sometimes up to as much as 20 millimeters. A number of such cannulas are inserted for any given operation.

A viewing instrument, typically including a miniature video camera, or optical telescope is inserted through one of these cannulas and a variety of surgical instruments and refractors are inserted through others. The image provided by the viewing device may be displayed on a video screen or television monitor, affording the surgeon enhanced visual control over the instruments. Because a commonly used viewing instrument is called an "endoscope," this type of surgery is often referred to as "endoscopic surgery." In the abdomen, endoscopic procedures are commonly referred to as laparoscopic surgery, and in the chest, as thoracoscopic surgery. Abdominal procedures may take place either inside the abdominal cavity (in the intraperitoneal space) or in a space created behind the abdominal cavity (in the retroperitoneal space). The retroperitoneal space is particularly useful for operations on the aorta and spine or abdominal wall hernia.

Minimally invasive surgery has virtually replaced open surgical techniques for operations such as cholecystectomy and anti-reflux surgery of the esophagus and stomach. This has not occurred in either peripheral vascular surgery or cardiovascular surgery. An important type of vascular surgery is to replace or bypass a diseased, occluded or injured artery. Arterial replacement or bypass grafting has been performed for many years using open surgical techniques and a variety of prosthetic grafts. These grafts are manufactured as fabrics (often from DACRON® (polyester fibers) or TEFLON® (fluorocarbon fibers)) or are prepared as autografts (from the patient's own tissues) or heterografts (from the tissues of animals) or a combination of tissues, semi-synthetic tissues and or alloplastic materials. A graft can be joined to the involved artery in a number of different positions, including end-to-end, end-to-side, and side-to-side. This attachment between artery and graft is known as an anastomosis. Constructing an arterial anastomosis is technically challenging for a surgeon in open surgical procedures, and is almost a technical impossibility using minimally invasive techniques.

Many factors contribute to the difficulty of performing arterial replacement or bypass grafting. See generally, Wylie, Edwin J. et al., Manual of Vascular Surgery, (Springer-Verlag New York), 1980. One such factor is that the tissues to be joined must be precisely aligned with respect to each other to ensure the integrity and patency of the anastomosis. If one of the tissues is affixed too close to its edge, the suture can rip through the tissue and impair both the tissue and the anastomosis. Another factor is that, even after the tissues are properly aligned, it is difficult and time consuming to pass the needle through the tissues, form the knot in the suture material, and ensure that the suture material does not become tangled. These difficulties are exacerbated by the small size of the artery and graft. The arteries subject to peripheral vascular and cardiovascular surgery typically range in diameter from several millimeters to several centimeters. A graft is typically about the same size as the artery to which it is being attached. Another factor contributing to the difficulty of such procedures is the limited time available to complete the procedure. The time the surgeon has to complete an arterial replacement or bypass graft is limited because there is no blood flowing through the artery while the procedure is being done. If blood flow is not promptly restored, sometimes in as little as thirty minutes, the tissue the artery supplies may experience significant damage, or even death (tissue necrosis). In addition, arterial replacement or bypass grafting is made more difficult by the need to accurately place and space many sutures to achieve a permanent hemostatic seal. Precise placement and spacing of sutures is also required to achieve an anastomosis with long-term patency.

Highly trained and experienced surgeons are able to perform arterial replacement and bypass grafting in open surgery using conventional sutures and suturing techniques. A suture has a suture needle that is attached or "swedged on" to a long, trailing suture material. The needle must be precisely controlled and accurately placed through both graft and artery. The trailing suture material must be held with proper tension to keep the graft and artery together, and must be carefully manipulated to prevent the suture material from tangling. In open surgery, these maneuvers can usually be accomplished within the necessary time frame, thus avoiding the subsequent tissue damage (or tissue death) that can result from prolonged occlusion of arterial blood flow.

The difficulty of suturing a graft to an artery using minimally invasive surgical techniques has effectively prevented the safe use of this technology in both peripheral vascular and cardiovascular surgical procedures. When a minimally invasive procedure is done in the abdominal cavity, the retroperitoneal space, or chest, the space in which the operation is performed is more limited, and the exposure to the involved organs is more restricted, than with open surgery. Moreover, in a minimally invasive procedure, the instruments used to assist with the operation are passed into the surgical field through cannulas. When manipulating instruments through cannulas, it is extremely difficult to position tissues in their proper alignment with respect to each other, pass a needle through the tissues, form a knot in the suture material once the tissues are aligned, and prevent the suture material from becoming tangled. Therefore, although there have been isolated reports of vascular anastomoses being formed by minimally invasive surgery, no system has been provided for widespread surgical use which would allow such procedures to be performed safely within the prescribed time limits.

As explained above, anastomoses are commonly formed in open surgery by suturing together the tissues to be joined. However, one known system for applying a clip around tissues to be joined in an anastomosis is disclosed in a brochure entitled, "VCS Clip Applier System", published in 1995 by Auto Suture Company, a Division of U.S. Surgical Corporation. A clip is applied by applying an instrument about the tissue in a nonpenetrating manner, i.e., the clip does not penetrate through the tissues, but rather is clamped down around the tissues. As previously explained, it is imperative in forming an anastomosis that tissues to be joined are properly aligned with respect to each other. The disclosed VCS clip applier has no means for positioning tissues. Before the clip can be applied, the tissues must first be properly positioned with respect to each other, for example by skewering the tissues with a needle as discussed above in common suturing techniques or with forceps to bring the tissues together. It is extremely difficult to perform such positioning techniques in minimally invasive procedures.

Therefore, there is currently a need for other tissue connector assemblies.

SUMMARY OF THE INVENTION

The present invention involves improvements to devices and methods for connecting tissues or tissue(s) and grafts, such as in a vascular anastomosis. The invention generally involves a surgical clip which is self-closing. Preferably, the surgical clip comprises a shape memory material, most preferably nitinol.

According to one aspect of the invention, a tissue connector assembly is provided with a clip movable between an open configuration and a closed configuration, and a mechanical restraining device attached to the clip for restraining the clip in its open configuration. The clip may have a generally U-shaped configuration when in its open configuration.

The mechanical restraining device may include a coil for biasing the clip in its open configuration. Alternatively, the clip may include a tubular wire and the mechanical restraining device may include an elongated member that is positionable within the tubular wire.

According to another aspect of the present invention, a tissue connector assembly generally comprises a clip having a spiral shaped configuration when in a closed configuration and an open configuration wherein the clip is configured to form less than a full 360 degree turn. The spiral may be formed in one plane or may extend from a plane of a first loop of the spiral to form a generally conical shaped helical clip. The spiral shaped configuration of the clip generally provides for tight compression of the connecting tissue and may reduce the amount of surface area of the clip exposed to blood flow in an anastomosis, for example.

A needle may be attached to the clip for piercing tissue/graft material, and may be releasably attached to facilitate removal of the needle after insertion of the clip. The clip is generally small enough to prevent obstruction of a surgeon's view of the tissue being connected and allow for precise control of the clip by the surgeon.

In another aspect of the invention, a locking device is provided for releasably locking the clip in its open configuration. Upon release of the locking device a restraining force is removed from the clip to allow the clip to move to its unbiased, closed position. Advantageously, the locking device may also be arranged to removably connect a needle to the clip. Upon release of the locking device, the needle is disconnected from the clip. Both removal of the needle and release of the biasing force from the clip may occur simultaneously.

A method of the present invention generally includes inserting a clip through tissue with the clip biased in an open position by a restraining device coupled to the clip, and removing the restraining force on the clip to allow the clip to close.

Another aspect of the present invention generally includes inserting a needle and a clip attached to the needle through tissue with an instrument, with the ability to remove the needle from the clip with the same instrument. The present invention may allow a surgeon to single handedly insert and close the clip to connect tissue using a minimum amount of instruments.

The above is a brief description of some deficiencies in the prior art and advantages of the present invention. Other features, advantages, and embodiments of the invention will be apparent to those skilled in the art from the following description, accompanying drawings, and claims.

BRIEF DESCRIPTION OF THE DRAWINGS

FIG. 1 is a front view of a tissue connector assembly of the present invention;

FIG. 2A shows a graft vessel connected to a target vessel with tissue connector assemblies of FIG. 1;

FIG. 2B is a front view of the connected graft and target vessels of FIG. 2A, with portions broken away to show detail;

FIG. 2C is an enlarged view of the tissue connection shown in FIG. 2B;

FIG. 3A is an enlarged view of a fastener of the tissue connector assembly of FIG. 1 shown in a closed position;

FIG. 3B is a side view of the fastener of FIG. 3A;

FIG. 3C is an enlarged view of the fastener in an open position;

FIG. 3D is an enlarged view of an alternate configuration of the fastener shown in a closed position;

FIG. 3E is an enlarged view of an alternate configuration of the fastener shown in a closed position;

FIG. 3F is a side view of the fastener of FIG. 3E;

FIG. 3G is an enlarged view of an alternate configuration of the fastener shown in a closed position;

FIG. 4A is a cross-sectional view of a restraining device of the tissue connector assembly of FIG. 1 in a locked position;

FIG. 4B is a cross-sectional view of the restraining device of FIG. 4A taken in the plane including line 4B-4B;

FIG. 4C is a cross-sectional view of the restraining device of FIG. 4A in an unlocked position;

FIG. 5 is an alternate embodiment of the restraining device of FIG. 4A;

FIG. 6 is a perspective of a second embodiment of a tissue connector assembly of the present invention;

FIG. 7 shows two tissue connector assemblies of FIG. 6 in a first step for connecting a graft vessel to a target vessel;

FIG. 8 shows a second step for connecting the graft vessel to the target vessel;

FIG. 9 shows a third step for connecting the graft vessel to the target vessel; and FIG. 10 shows an alternate method for connecting the graft vessel to the target vessel with the tissue connector assemblies of FIG. 6.

Corresponding reference characters indicate corresponding parts throughout the several views of the drawings.

DESCRIPTION OF THE INVENTION

Referring now to the drawings, and first to FIG. 1, a tissue connector assembly constructed according to the principles of the present invention is shown and generally indicated with reference numeral 1. The tissue connector assembly 1 may be used to manipulate and align tissues, or tissue and graft with respect to each other and thereafter connect the tissues together (FIGS. 2A-2C). As used herein, the term graft includes any of the following: homografts, xenografts, allografts, alloplastic materials, and combinations of the foregoing. The tissue connector assembly 1 may be used in vascular surgery to replace or bypass a diseased, occluded, or injured artery by connecting a graft vessel 12 to a coronary artery 14 or vein in an anastomosis, for example. The tissue connector assembly 1 may be used in open surgical procedures or in minimally invasive or endoseopic procedures for attaching tissue located in the chest, abdominal cavity, or retroperitoneal space. These examples, however, are provided for illustration and are not meant to be limiting.

In the embodiment shown in FIG. 1, the tissue connector assembly 1 generally comprises a penetrating member 2, and fastener or surgical clip 10 (FIG. 1). A restraining device, generally indicated at 8 and comprising a spring (or coil) 26 and a locking device generally indicated at 4, is connected to the fastener 10 for holding the fastener in a deformed configuration as further described below.

The penetrating member or needle 2 has a sharp pointed tip 30 at its distal end for penetrating tissue. The needle 2 may be bent as shown in FIG. 1, for example. The distal end of the needle 2 is preferably rigid to facilitate penetration of tissue. The remaining length of the needle 2 may be rigid or flexible to facilitate movement of the needle through the tissue as further described below. The tip 30 of the needle 21 may be conical, tapered, or grounded to attain a three or four facet tip, for example. The needle 2 may be made from stainless steel or any other suitable material, such as a polymeric material. It is to be understood that the needle 2 may have a shape or radius of curvature other than the one shown, without departing from the scope of the invention. The needle 2 may be integrally formed with the locking device 4 or may be swaged, welded, threadably attached, or attached by any other suitable means to the locking device.

As shown in FIG. 3A, one embodiment of a fastener 10 comprises a deformable wire 34 made of a shape memory alloy. A nickel titanium (nitinol) based alloy may be used, for example. The nitinol may include additional elements which affect the yield strength of the material or the temperature at which particular pseudoelastic or shape transformation characteristics occur. The transformation temperature may be defined as the temperature at which a shape memory alloy finishes transforming from martensite to austenite upon heating (i.e., $A_f$ temperature). The shape memory alloy preferably exhibits pseudoelastic (superelastic) behavior when deformed at a temperature slightly above its transformation temperature. At least a portion, of the shape memory alloy is converted from its austenitic phase to its martensitic phase when the wire is in its deformed configuration. As the stress is removed, the material undergoes a martensitic to austenitic conversion and springs back to its original undeformed configuration. When the wire 34 is positioned within the tissue in its undeformed configuration, a residual stress is present to maintain the tissue tightly together (FIG. 2C). In order for the pseudoelastic wire 34 to retain sufficient compression force in its undeformed configuration, the wire should not be stressed past its yield point in its deformed configuration to allow complete recovery of the wire to its undeformed configuration. The shape memory alloy is preferably selected with a transformation temperature suitable for use with a stopped heart condition where cold cardioplegia has been injected for temporary paralysis of the heart tissue (e.g., temperatures as low as 8-10 degrees Celsius).

It is to be understood that the shape memory alloy may also be heat activated, or a combination of heat activation and pseudoelastic properties may be used, as is well known by those skilled in the art.

The cross-sectional diameter of the wire 34 and length of the wire will vary depending on the specific application. The diameter "d" of the wire 34 may be, for example, between 0.001 and 0.015 inch. For coronary bypass applications, the diameter is preferably between 0.001 and 0.008 inch with a diameter "D" of the loop being between 0.0125 and 0.0875 inch (FIG. 3A). The diameter "D" of the loop of the fastener 120 in its closed position is preferably sized to prevent movement between adjacent tissues. As shown in FIG. 3A, the wire 34 has a circular cross-sectional shape. It is to be understood that the wire may have other cross-sectional shapes such as rectangular, or may be formed from multiple strands without departing from the scope of the invention.

The proximal end of the wire 34 may include a stop 36 having a cross-sectional area greater than the cross-sectional area of the wire and coil 26 to prevent the wire and coil from passing through the tissue (FIG. 3C). The stop 36 may be attached to the end of the wire 34 by welding, gluing or other suitable attachment means or may be formed integrally with the wire by deforming the end of the wire. The stop 36 may also be eliminated to facilitate pulling the fastener completely through the tissue, if, for example, the entire fastener needs to be removed from the vessel during the insertion procedure. The distal end of the wire 34 includes an enlarged portion 38 for engagement with the restraining device 8 as further described below (FIG. 4A). The enlarged portion 38 may be formed by deforming the end of the wire 34 by swaging or arc welding, or attaching by welding, swaging, or other suitable means to form an enlarged portion at the end of the wire.

The wire 34 has an undeformed or closed position (state of configuration) (FIG. 3A) for keeping or connecting tissue together, and a deformed or open position (state or configuration) (FIG. 3C) for insertion of the wire into tissue. The wire 34 is preferably not deformed past its yield point in its open position. Accordingly, it may have a U-shaped configuration in its open position to facilitate insertion of the wire 34 through the tissue. It is to be understood that a U-shaped configuration may be alternatively substituted by an equivalent structure such as C-shaped, V-shaped, J-shaped, and other similarly shaped configurations. The wire 34 is moved from its closed position to its open position by the restraining device 8, as further described below. When in its closed position, the wire 34 forms a loop with the ends of the wire in a generally side-by-side or overlapping orientation (FIG. 3B).

The wire 34 may be formed in the above described shape by first wrapping the wire onto a mandrel and heat treating the wire at approximately 400-500 degrees Celsius for approximately 5 to 30 minutes. The wire 34 is then air quenched at room temperature. The mandrel may have a constant diameter or may be conical in shape.

An alternate configuration of the surgical clip 10 in its closed position is shown in FIG. 3D, and generally indicated at 40. The fastener 40 forms a spiral configuration in its closed position for trapping tissue within a loop formed by the spiral. In its open position, the fastener 40 is configured to form less than a full 360 degree turn.

Another alternate configuration of the surgical clip 10 is shown in FIGS. 3E and 3F in its closed position, and is generally indicated at 41. The fastener 41 is formed in a spiral about a central longitudinal axis A. As shown in FIG. 3F, the fastener 41 has a generally conical shape along the longitudinal axis A, with a decreasing diameter as the radius of curvature of the fastener 41 decreases. The fastener 41 has an inner end portion 45 and an outer end portion 47, with the enlarged portion 38 of the wire being disposed at the outer end portion for engagement with the restraining device 8 (FIG. 3E).

A modification of the fastener is shown in FIG. 3G, and generally indicated at 43. The fastener 43 is same as the fastener 41 described above, except that the enlarged portion 38, which is adapted for engaging a restraining device or releasable mechanism, is positioned at the inner end portion 45 of the fastener. Placement of the restraining device 8 at the inner end portion 45 of the fastener 43 increases the compression force of the wire in its undeformed position on the tissue and decreases the surface area of the fastener exposed to blood flow.

It is to be understood that the fastener 10, 40, 41, 43 may have undeformed or deformed configurations different than those shown herein without departing from the scope of the invention. In addition, a locking clip (not shown) may also be attached to connect the ends of the fastener 10, 40, 41, 43 when the fastener is in its closed position to prevent possible opening of the fastener over time. The locking clip may also be integrally formed with one end of the fastener.

As shown in FIG. 3C, the wire 34 is surrounded by the spring or coil 26 which, along with the locking device 4, restrains the wire in its deformed configuration. The coil 26 comprises a helical wire forming a plurality of loops which define a longitudinal opening 44 for receiving the shape memory alloy wire 34. The coil 26 may be formed from a platinum alloy wire having a cross-sectional diameter of approximately 0.0005-0.005 inch, for example. The wire may have other cross-sectional shapes and be formed of different materials. The coil 26 is preferably sized so that when in its free (uncompressed state) it extends the length of the wire 34 with one end adjacent the stop 36 at the proximal end of the wire and the other end adjacent the enlarged portion 38 at the distal end of the wire (FIG. 3B). It is to be understood that the spring 26 may not extend the full length of the wire. For example, a flange or similar device may be provided on an intermediate portion of the wire 34 to limit movement of the coil along the length of the wire.

When the coil 26 is in its free state (with the wire 34 in its undeformed configuration), loops of the coil are generally spaced from one another and do not exert any significant force on the wire 34 (FIG. 3A). When the coil 26 is compressed (with the wire 34 in its deformed configuration), loops of the coil on the inner portion 46 of the coil are squeezed together with a tight pitch so that the loops are near or contiguous with one another while loops on the outer portion 48 of the coil are spaced from one another (FIG. 3C). This is due to the compressed inner arc length of the coil 26 and the expanded outer arc length of the coil. The compression of the loops on the inner portion 46 of the coil 26 exerts a force on the inner side of the wire 34 which forces the wire to spread open (i.e., tends to straighten the wire from its closed configuration to its open configuration). The end of the coil 26 adjacent the stop 36 is held in a fixed position relative to the wire 34. The opposite end of the coil 26 is free to move along the wire 34 and is held in place when the coil is in its compressed position by the locking device 4 (FIG. 4A).

The locking device 4 shown in FIGS. 1 and 4A-4C comprises a flexible tubular member 50 having a distal end portion 52 coupled to a needle 2 and a proximal end portion 54 releasably attached to the wire 34. The tubular member 50 is movable between a locked position (FIG. 4A) for holding the coil 26 in its compressed position and the wire 34 in its deformed position, and an unlocked position (FIG. 4C) for inserting or releasing the wire and coil. Three slots 58 are formed in the tubular member 50 extending from the proximal end 54 of the member and along at least a portion of the member (FIGS. 4B and 4C). The slots 58 are provided to allow the proximal end 54 of the tubular member 50 to open for insertion and removal of the wire 34 when the tubular member is in its unlocked position (FIG. 4C). It is to be understood that the number of slots 58 and configuration of the slots may vary.

The proximal end 54 of the tubular member 50 includes a bore 62 having a diameter slightly greater than the outer diameter d of the wire 34, but smaller than the diameter of the enlarged portion 38, and smaller than the outer diameter of the coil 26. The bore 62 extends into a cavity 64 sized for receiving the enlarged portion 38 of the wire 34. Member 50 may be described as having an annular flange 61 for releasably securing the enlarged portion 38. As shown in FIG. 4C, upon application of an inwardly directed radial squeezing force on the tubular member 50 the proximal end 54 of the tubular member is opened to allow for insertion or removal of the wire 34. When the force is released (FIG. 4A), the tubular member 50 moves back to its locked position and securely holds the wire 34 in place and compresses the coil 26. A disc 51 may be inserted into the tubular member 50 to act as a fulcrum and cause the proximal end 54 of the tubular member to open upon application of force on the tubular member. Alternatively, the disc 51 may be integrally formed with the tubular member 50. As shown in FIG. 4A, the length l of the bore 62 or flange 61 determines the amount of compression of the coil, which in turn determines the amount of deformation of the wire 34. The greater the length l of the bore 62, the greater the compression of the coil 26 and the more straightening the wire 34 will undergo. The compression of the coil 26 is preferably limited so that the wire 34 is not stressed beyond its yield point. This allows the wire 34 to revert back to its original undeformed configuration and apply sufficient pressure to hold the connected tissue together.

An alternate embodiment of the restraining device is shown in FIG. 5, and generally indicated with reference numeral 70. The restraining device 70 is used with a tubular (hollow) shape memory alloy wire or tube 72 and comprises an elongated member (or mandrel) 74 sized for insertion into the wire. The mandrel 74 is preferably formed from a material which is stiffer than the material of the wire 72 so that upon insertion of the mandrel into the wire, the wire is deformed into its open position. The restraining device 70 includes a stop 76 located at the proximal end of the wire 72. The stop operates to prevent the fastener from being pulled through the tissue, and limits axial movement of the mandrel 74 in the proximal direction (to the right as viewed in FIG. 5). The distal end of the mandrel 74 is releasably attached to the needle 2. It is to be understood that other types of restraining devices may be used without departing from the scope of the invention.

It is to be understood that locking devices other than those described above may be used without departing from the scope of the invention. For example, a locking device (not shown) may comprise a tubular member having an opening formed in a sidewall thereof for receiving an end portion of the wire. The end of the wire may be bent so that it is biased to fit within the opening in the sidewall of the tubular member. An instrument, such as a needle holder may then be used to push the wire away from the opening in the tubular member and release the wire from the tubular member. Various other types of locking devices including a spring detent or bayonet type of device may also be used.

Another embodiment of the tissue connector assembly is shown in FIG. 6 and generally indicated with reference numeral 110. The tissue connector assembly 110 is similar to the tissue connector assembly 1 of the first embodiment, except that a flexible member 118 is inserted between a restraining device 124 and needle 116. FIG. 6 shows the tissue connector assembly 110 with a fastener 120 in an open (deformed) position. The fastener 120 may be the same as the fasteners 10, 40, 41, 43 described above and shown in FIGS. 3A-3G for the tissue connector assembly 1 of the first embodiment, for example. The fastener 120 includes the restraining device 124 comprising a coil 126 and a locking device 128. The locking device 128 is same to the locking device 4 described above and shown in FIGS. 4A-4C, except that the distal end is configured for attachment to the flexible member 118.

The flexible member 118 is attached to the distal end of the locking device 128 with a tapered portion or transition sleeve 156 extending from the locking device to the flexible member 118 to facilitate insertion of the locking device through tissue. The tapered sleeve 156 is preferably sufficiently curved to facilitate movement of the tissue connector assembly 110 through connecting tissue in an anastomosis, for example. The sleeve 156 may be formed from a metal alloy such as stainless steel or a suitable polymeric material. The needle 116 may be swaged into the sleeve 156, or a heat shrink plastic covering may hold the needle in place. The locking device 128 may also be curved.

The flexible member 118 may be in the form of a suture formed from conventional filament material, metal alloy such as nitinol, polymeric material, or any other suitable material. The material may be non-stretchable or stretchable, solid or hollow, and have various cross-sectional diameters. The suture may have a cross-sectional diameter of 0.003 inch, for example. The diameter and length of the suture will vary depending on the specific application. The suture may be attached to the needle 116 by crimping or swaging the needle onto the suture, gluing the suture to the needle, or any other suitable attachment method. The flexible member 118 may have cross-sectional shapes other than the one shown herein.

The needle 116 may be integrally formed with the flexible member 118. The diameter of at least a portion of the needle 116 is preferably greater than the diameter of the flexible member 118 so that the flexible member can easily be pulled through an opening formed in the tissue by the needle.

As noted above, the tissue connector assemblies 1, 110 of this invention have many uses They may be especially useful in minimally invasive surgical procedures including creating an anastomosis between a vascular graft 12 and an artery 14 (FIGS. 2A-2C). The anastomosis may be used to replace or bypass a diseased, occluded or injured artery. A coronary bypass graft procedure requires that a source of arterial blood flow be prepared for subsequent bypass connection to a diseased artery. An arterial graft may be used to provide a source of blood flow, or a free graft may be used and connected at the proximal end to a source of blood flow. Preferably, the source of blood flow is one of any number of existing arteries which may be dissected in preparation for the bypass graft procedure. In many instances it is preferred to use the left internal mammary artery (LIMA) or the right internal mammary artery (RIMA), for example. Other vessels which may be used include the saphenous vein, gastroepiploic artery in the abdomen, radial artery, and other arteries harvested from the patient's body as well as synthetic graft materials, such as DACRON® or GORETEX® (expanded polytetrafluoroethylene). If a free graft vessel is used, the upstream end of the dissected vessel, which is the arterial blood source, will be secured to the aorta to provide the desired bypass blood flow, as is well known by those skilled in the art. The downstream end of the graft vessel is trimmed for attachment to an artery, such as the left anterior descending coronary (LAD). It is to be understood that the anastomosis may be formed in other vessels or tissue.

FIGS. 2A-2C and 7-9 show an exemplary use of the tissue connector assemblies 1, 110 for connecting a graft vessel 12 to an artery 14 (target vessel). In this example, two tissue connector assemblies 110 (FIG. 6) are used to make connections at generally opposite sides of the graft vessel and a plurality of tissue connector assemblies 1 (FIG. 1) are used to make connections between those made with tissue connector assemblies 110. The procedure may be accomplished with a beating heart procedure with the use of a heart stabilizer to keep the heart stable, for example. The procedure may also be performed endoscopically.

The patient is first prepped for standard cardiac surgery. After exposure and control of the artery 14, occlusion and reperfusion may be performed as required. Referring to FIGS. 7-9, after the arteriotomy of the snared graft vessel 12 has been made to the appropriate length, a tissue connector assembly 110 is attached to the free end of the graft vessel along an edge margin of the vessel. In order to attach the connector assembly 110, the surgeon grasps the needle 116 with a needle holder (e.g., surgical pliers, forceps, or any other suitable instrument) and inserts the needle 116 into an end margin of the graft vessel 12 in a direction from the exterior of the vessel to the interior of the vessel. The surgeon then releases the needle 116 and grasps a forward end of the needle which is now located inside the graft vessel 12 and pulls the needle and a portion of the suture 118 through the vessel. The needle 116 is passed through an opening 121 formed in the sidewall of the artery 14 and inserted into the tissue of the artery in a direction from the interior of the artery to the exterior of the artery. The surgeon then grasps the needle 116 located outside the artery 14 and pulls the needle and a portion of the suture 118 through the arterial wall. A second tissue connector assembly 110 may be inserted at a location generally 180 degrees from the location of the first tissue connector in a conventional "heel and toe" arrangement. Alternatively, a number of tissue connectors 110 may be inserted generally around the location of the heel. The graft vessel 12 may then be pulled towards the artery 14 to determine whether the opening 121 formed in the sidewall of the artery is large enough before completing the anastomosis.

Once the tissue connector assemblies 110 are inserted, the graft vessel 12 is positioned above the opening 121 in the sidewall of the artery 14 (FIG. 7). The fasteners 120 and needles 116 are pulled generally away from the artery 14 to reduce the length of the suture 118 between the vessel 12 and artery and "parachute" the vessel onto the artery (FIG. 8). The needles 116 are then pulled away from the artery 14 until the fastener 120 is positioned within the graft vessel 12 and artery with one end of each fastener extending from the vessel and the opposite end of each fastener extending from the artery (FIG. 9). The edges of the graft vessel 12 and artery 14 are positioned adjacent one another to form a continuous interior and exterior surface along the mating portions of the vessel and artery. As shown in FIG. 2C, the tissue is compressed within the fastener 120.

A surgical instrument (e.g., needle holder) is used to radially squeeze each locking device 128 to release the locking device from the fastener 120. Upon removal of the locking device 128, the coil 126 moves to its free uncompressed state which allows the wire 134 to return to its original undeformed closed position (FIG. 2A). As the wires 134 move to their closed position the adjacent tissues of the graft vessel 12 and artery 14 which were previously pulled together during the parachuting of the graft vessel onto the artery, are squeezed together to securely engage the graft vessel and artery (FIGS. 2B and 2C).

The tissue connector assemblies 1 are subsequently inserted at circumferentially spaced locations around the periphery of the graft vessel 12 to sealingly fasten the graft vessel to the artery 14. The needle 2 of the fastener 1 is inserted into the graft vessel 12 from the exterior surface of the graft vessel and pushed through the graft vessel and artery 14 tissue. The needle holder is then used to pull the needle 2 through the arterial wall. An instrument (same needle holder or other suitable instrument) is used to apply a squeezing force to the locking device 4 to release the wire 34 and coil 26 from the needle 2. This allows the coil 26 to move to its uncompressed configuration and the wire 34 to move to its closed position. It should be noted that the tissue connector assemblies 110 may remain in their open position while the tissue connector assemblies 1 are inserted into the tissue and moved to their closed position. The locking devices 128 of the tissue connector assemblies 110 may subsequently be removed from the fasteners 120 to allow the fasteners to move to their closed position. The number and combination of tissue connectors assemblies 1, 110 required to sealingly secure the connecting tissues together may vary. For example, only tissue connector assemblies 1 may be used to complete the entire anastomosis, or only tissue connector assemblies 110 may be used to connect tissues.

It should be noted that as the locking device 4 is squeezed two steps are accomplished. The fastener 10 is released from the locking device 4, thus allowing the coil 26 to uncompress and the wire 34 to move to its closed configuration, and the needle 2 is released from the fastener. Thus, in the embodiment shown, the locking device 4 provides for simultaneous actuating closure of the fastener 10 and release of the needle 2 from the fastener.

The graft vessel 12 may also be parachuted onto the artery 14 in the method shown in FIG. 10. The needles 116 are inserted into the graft vessel 12 and artery 14 as described above and the sutures 118 are pulled through the vessel so that the fasteners 120 are positioned within the vessel. The needles 116 are then pulled away from the artery 14 to "parachute" the graft vessel 12 onto the artery.

Although the coil 126 is shown as remaining on the wire (FIG. 6), it is to be understood that the coil 126 may also be removed from the wire 134, leaving only the wire in the connected tissue.

Although the suturing procedure has been described for an end-to-side anastomosis, it should be appreciated that the procedure is applicable to an end-to-end and side-to-side anastomosis, connecting various tissue structures including single and multiple tissue structures, and puncture sites, and connecting tissue to a prosthetic graft or valve, for example.

It will be observed from the foregoing that the tissue connector assemblies of the present invention have numerous advantages. Importantly, the assemblies are easier and faster to apply than conventional sutures which require tying multiple knots. The assemblies may be used in minimally invasive procedures including endoscopic procedures, and may be inserted single handedly.

All references cited above are incorporated herein by reference.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. A tissue connector assembly comprising a self-closing clip movable between an open configuration and a closed configuration, said clip having a generally U-shaped configuration when in said open configuration, and a mechanical restraining device coupled to said clip for restraining said clip in said open configuration, wherein said restraining device is coupled to said clip such that in at least one state of said restraining device, an entirety of said restraining device moves with movement of said clip in response to a movement force applied to said clip, and further wherein said clip assumes a spiral configuration in said closed configuration.

2. The tissue connector assembly of claim 1 further comprising a needle releasably attached to said clip.

3. The tissue connector assembly of claim 1 wherein at least a portion of said mechanical restraining device remains on said clip when said needle is released from said clip.

4. The tissue connector assembly of claim 1 wherein said clip comprises a wire.

5. The tissue connector assembly of claim 4 wherein said wire is tubular.

6. The tissue connector assembly of claim 4 wherein said wire has a generally circular cross-section.

7. The tissue connector assembly of claim 4 wherein said wire comprises shape memory material.

8. The tissue connector assembly of claim 4 wherein said wire has a first end portion, a second end portion and an elongated member therebetween, said first end portion being coupled to said mechanical restraining device, said second end portion having a cross-sectional area greater than a cross-sectional area of said elongated member.

9. The tissue connector assembly of claim 1 wherein said clip is in a relaxed state when in said closed configuration.

10. The tissue connector assembly of claim 1 wherein said mechanical restraining device comprises a coil surrounding at least a portion of said clip.

11. The tissue connector assembly of claim 10 wherein said coil comprises a plurality of adjacent loops, said coil being compressible with said plurality of adjacent loops being spaced closer to one another along one side of said coil than along an opposite side of said coil.

12. The tissue connector assembly of claim 10 wherein said mechanical restraining device includes a lock releasably engaging said coil, wherein engagement of said lock with said coil biases said clip in said open configuration.

13. The tissue connector assembly of claim 1 wherein said clip comprises a tubular wire and said mechanical restraining device comprises an elongated member positioned in said wire.

14. A tissue connector assembly comprising a self-closing clip having an open configuration and a closed configuration and a coil wound about said clip, wherein said coil is adapted to provide a biasing force to bias said clip in said open configuration, and further wherein a relationship of a longitudinal length of said coil relative to a longitudinal length of said clip differs between said open configuration and said closed configuration.

15. The tissue connector assembly of claim 14 further comprising a needle coupled to said clip.

16. The tissue connector assembly of claim 15 wherein said needle is releasably coupled to said clip.

17. The tissue connector assembly of claim 14 wherein said clip has a generally U-shaped configuration when in said open configuration.

18. The tissue connector assembly of claim 14 wherein said coil surrounds at least a portion of said clip and is arranged to bias said clip in said open configuration.

19. A tissue connector assembly comprising a clip having an open configuration and a closed configuration and a restraint coupled to said clip when in said open configuration, wherein said clip assumes a spiral configuration in said closed configuration, wherein said restraint comprises an elongated member removably insertable into said clip, said clip and said elongated member configured such that said clip assumes said open configuration when said elongated member is inserted into said clip, and said clip transitions to said spiral configuration with removal of said elongated member from said clip.

20. The tissue connector assembly of claim 19 further comprising a needle coupled to said clip.

21. The tissue connector assembly of claim 20 wherein said needle is releasably coupled to said clip.

22. The tissue connector assembly of claim 19 wherein said clip comprises a tubular member and said elongated member is sized for insertion into said tubular member.

23. A tissue connector assembly comprising a clip having an open configuration and a closed configuration and a restraint coupled to said clip when in said open configuration, wherein said clip assumes a spiral configuration in said closed configuration, wherein said clip has a generally U-shaped configuration defined by a continuous, single bend direction along an entire length of said clip when in said open configuration.

24. A tissue connector assembly comprising a clip movable between an open configuration and a closed configuration, said clip having a spiral shaped configuration when in said closed configuration, and an open configuration in which said clip is configured to form less than a full 360 degree turn in extension between opposing terminal ends, wherein said clip has a generally U-shaped configuration when in said open configuration.

25. The tissue connector assembly of claim 24 wherein said clip spirals around a central longitudinal axis when in said closed configuration, said clip having a generally conical shape along said longitudinal axis.

26. The tissue connector assembly of claim 25 wherein said clip has an inner end and an outer end, said inner end having a smaller radius than said outer end, said inner end being coupled to a needle.

27. The tissue connector assembly of claim 24 further comprising a needle releasably attached to said clip.

28. A tissue connector assembly comprising:
a surgical clip having a relaxed state;
a needle having a sharp distal point;
a connector releasably coupling said needle to said clip; and
a biasing member associated with said surgical clip;
wherein said connector, when coupling said needle to said clip, urges said biasing member to bias said clip away from said relaxed state.

29. The tissue connector assembly of claim 28, wherein said connector comprises a portion forming a recess, and said clip comprises a portion which adapted to mate with said recess.

30. The tissue connector assembly of claim 29, wherein said biasing member comprises a coil surrounding at least a portion of said clip, said coil including a first end restrained from movement in one direction along said clip, and a second movable end, wherein said coupling of said connector with said needle compresses said coil by movement of said second end.

31. A tissue connector assembly comprising a needle, a clip, and a locking device releasably connecting said needle to said clip, said locking device being movable between an open position for insertion and removal of said needle and a closed position for coupling said needle to said clip and biasing said clip in an open configuration.

32. The tissue connector assembly of claim 31 wherein said clip comprises a wire.

33. The tissue connector assembly of claim 32 wherein said wire comprises shape memory material.

34. The tissue connector assembly of claim 31 further comprising a spring for biasing said clip in said open configuration.

35. A method for connecting multiple portions of material, at least one of which comprises tissue, comprising:
inserting a clip formed of a wire having opposing first and second terminal tips, which is spring biased away from a closed configuration to an open configuration, through said multiple portions of material, at least one of which comprises tissue, including initially inserting said first tip into said multiple portions of material before any other segment of said clip;
mechanically maintaining said clip in said open configuration while inserting said clip through said materials; and
allowing said clip to return to said closed configuration and secure a portion of said material therein.

36. The method of claim 35 including maintaining said clip in said open configuration with a locking device.

37. The method of claim 35 wherein said clip is allowed to return to said closed configuration by disengaging said locking device.

38. The method of claim 37 wherein said clip includes a needle coupled to said locking device and said locking device is disengaged by decoupling said needle from said locking device.

39. The method of claim 35 wherein said clip is inserted through a layer of tissue and a layer of graft material.

40. A method for connecting multiple portions of material, at least one of which comprises tissue, said method comprising:
inserting a needle having a clip attached thereto through said multiple portions with a needle holder, wherein said needle is initially inserted into said multiple portions followed by said clip, including pulling said needle through said multiple portions with said needle holder; and
removing said needle from said clip with said needle holder, including removing a locking device holding said clip in an open position.

41. The method of claim 40 wherein said removing a locking device comprises applying an inwardly directed radial force to said locking device.

42. The method of claim 40 wherein said removing a locking device comprises uncompressing a coil biasing said clip in said open position.

43. The method of claim 40, wherein said inserting said needle includes grasping, releasing, and re-grasping said needle with said needle holder.

* * * * *